United States Patent [19]

Dobak, III et al.

[11] Patent Number: 5,787,715
[45] Date of Patent: Aug. 4, 1998

[54] MIXED GAS REFRIGERATION METHOD

[75] Inventors: John D. Dobak, III, San Diego, Calif.; Ray Radebaugh; Marcia L. Huber, both of Louisville, Colo.; Eric D. Marquardt, Lakewood, Colo.

[73] Assignees: Cryogen, Inc., San Diego, Calif.; The United States of America as represented by the Secretary of Commerce, Washington, D.C.

[21] Appl. No.: 698,044

[22] Filed: Aug. 15, 1996

Related U.S. Application Data

[63] Continuation-in-part of Ser. No. 542,123, Oct. 12, 1995.

[51] Int. Cl.$^6$ .................................................. F25B 19/02
[52] U.S. Cl. ................................................ 62/51.2; 62/114
[58] Field of Search ................................. 62/51.2, 114

[56] References Cited

U.S. PATENT DOCUMENTS

| | | | |
|---|---|---|---|
| 3,272,203 | 9/1966 | Chato | 128/303.1 |
| 3,273,356 | 9/1966 | Hoffman | 62/51.2 |
| 3,298,371 | 1/1967 | Lee | 62/293 |
| 3,398,738 | 8/1968 | Lamb et al. | 128/303.1 |
| 3,439,680 | 4/1969 | Thomas, Jr. | 128/303.1 |
| 3,477,434 | 11/1969 | Hood, Jr. et al. | 128/303.1 |
| 3,536,075 | 10/1970 | Thomas, Jr. | 128/303.1 |
| 3,662,755 | 5/1972 | Rautenbach et al. | 128/303.1 |
| 3,913,581 | 10/1975 | Ritson et al. | 128/303.1 |
| 4,015,606 | 4/1977 | Mitchiner et al. | 62/293 |
| 4,207,897 | 6/1980 | Lloyd et al. | 128/303.1 |
| 4,377,168 | 3/1983 | Rzasa et al. | 128/303.1 |

(List continued on next page.)

FOREIGN PATENT DOCUMENTS

| | | |
|---|---|---|
| 0 271 989 | 11/1990 | European Pat. Off. . |
| 2 477 406 | 9/1981 | France . |
| 0 839 516 | 6/1981 | U.S.S.R. . |
| 1 774 140 | 11/1992 | U.S.S.R. . |
| 1 336 892 | 11/1973 | United Kingdom . |
| 2 080 117 | 2/1982 | United Kingdom . |

OTHER PUBLICATIONS

Coxeter, Ruth; *Developments to Watch—The Deep Freeze for Irregular Hearbeats*; p. 90; Sep. 19, 1994; Business Week.

Friend, Daniel G.; *Thermophysical Property Computer Packages from NIST*; pp. 13–18; 1992; ASME HTD vol. 225, Computerized Thermophysical Property Packages.

Gage, Andrew A.; *Current Progress in Cryosurgery*; pp. 483–486; Mar. 28, 1988; American College of Cryosurgery, 8th Annual Meeting.

(List continued on next page.)

*Primary Examiner*—Christopher Kilner
*Attorney, Agent, or Firm*—Gerald W. Spinks

[57] ABSTRACT

A miniature mixed gas refrigeration system and method of operation are disclosed, having a coaxial catheter with an inner high pressure supply lumen and an outer low pressure return lumen. An optimum gas mixture is formulated from a group of component fluids, according to calculated thermodynamic properties of a group of candidate fluid mixtures. The gas mixture is pressurized by a compressor to a pressure less than 420 psia, for safety reasons. The distal portion of the outer lumen contains a micro-miniature heat exchanger constructed of laminated plates or sheets. The plates or sheets establish high pressure and low pressure passageways, with high surface area, having a tortuous path for the gas flow to maximize heat exchange. The high pressure outlet of the heat exchanger is connected to a Joule-Thomson expansion element where the high pressure gas is expanded isenthalpically to a lower temperature at least as low as 183K. This low temperature gas cools a heat transfer element mounted in the outer wall of the catheter, to cool an external object. Return gas flows back through the heat exchanger to pre-cool the incoming high pressure gas mixture.

20 Claims, 23 Drawing Sheets

U.S. PATENT DOCUMENTS

| | | | |
|---|---|---|---|
| 4,781,033 | 11/1988 | Steyert et al. | 62/51.2 |
| 5,078,713 | 1/1992 | Varney | 606/23 |
| 5,101,894 | 4/1992 | Hendricks | 62/51.2 |
| 5,139,496 | 8/1992 | Hed | 606/23 |
| 5,147,355 | 9/1992 | Friedman et al. | 606/23 |
| 5,275,595 | 1/1994 | Dobak, III | 606/23 |
| 5,281,212 | 1/1994 | Savage et al. | 606/15 |
| 5,281,213 | 1/1994 | Milder et al. | 606/15 |
| 5,281,215 | 1/1994 | Milder | 606/20 |
| 5,281,217 | 1/1994 | Edwards et al. | 606/41 |
| 5,324,286 | 6/1994 | Fowle | 606/23 |
| 5,337,572 | 8/1994 | Longsworth | 62/51.2 |
| 5,365,750 | 11/1994 | Greenthal | 62/51.2 |
| 5,423,807 | 6/1995 | Milder | 606/20 |

OTHER PUBLICATIONS

Hill, Dennis; *Throttle Cycle Cooler Vibration Characterization*; 5 pages; date of publication unknown; place of publication unknown.

Hubbell, Richard H.; *New Heat Transfer and Friction Factor Design Data for Perforated Plate Heat Exchangers*; pp. 383–390; 1988; Advanced Cryogenic Engineering, vol. 33.

Jichuan, Hu; *Heat Transfer Characteristics of a Perforated Plate: Part II—Heat Transfer Coefficients for the Separate Working Surfaces*; pp. 318–322; Sep., 1990; Cryogenics, vol. 30.

Jones, Jack A.; *Cryogenic Mixed Fluid Application Study and Computer Code Development, Final Report*; pp. i–18; date of publication unknown; place of plublication unknown.

Khatri, Ajay; *A Throttle Cycle Cryocooler Operating with Mixed Gas Refrigerants in 70K to 120K Temperature Range*; 5 pages; date of publication unknown; place of publication unknown.

Khatri, Ajay; *A Throttle Cycle Refrigerator Operating Below 77K*; 8 pages; date of publication unknown; place of publication unknown.

Little, W. A.; *Advances in Joule–Thomson Cooling*; pp. 1–10; date of publication unknown; place of publication unknown.

Venkatarathnam, G.; *Heat Transfer and Flow Friction Correlations in Perforated Plate Matrix Heat Exchangers*; pp. 313–317; Sep. 1990; Cryogenics, vol. 30.

Venkatarathnam, G.; *Matrix Heat Exchangers and Their Application in Cryogenic Systems*; pp. 907–918; Nov., 1990; Cryogenics, vol. 30.

First list of abstracts related to perforated plate heat exchangers, compiled for the applicant through a computer data base search; list not published.

Second list of abstracts related to perforated plate heat exchangers, compiled for the applicant through a computer data base search; list not published.

| Components: R124; R32; NF3; Kr | | | | |
|---|---|---|---|---|
| Compositions (mol fractions): 0.10; 0.20; 0.10; 0.60 | | | | |
| Low pressure= | 1.00000000000000 | bar | | |
| High pressure= | 21.00000000000000 | bar | | |

| Temp (K) | LowH (kJ/mol) | HighH (kJ/mol) | deltaH (kJ/mol) | deltaH* () |
|---|---|---|---|---|
| 150 | -12.9946 | -18.1647 | 5.1702 | 0.4334 |
| 155 | -12.6208 | -17.8633 | 5.2425 | 0.4395 |
| 160 | -12.2699 | -17.5574 | 5.2876 | 0.4432 |
| 165 | -11.9152 | -17.2473 | 5.3321 | 0.4470 |
| 170 | -11.5337 | -16.9329 | 5.3992 | 0.4526 |
| 175 | -11.1022 | -16.6141 | 5.5119 | 0.4620 |
| 180 | -10.5953 | -16.2907 | 5.6954 | 0.4774 |
| 185 | -9.98547 | -15.9623 | 5.9768 | 0.5010 |
| 190 | -9.24764 | -15.6285 | 6.3809 | 0.5349 |
| 195 | -8.37088 | -14.5635 | 6.1926 | 0.5191 |
| 200 | -7.37719 | -13.2504 | 5.8732 | 0.4923 |
| 205 | -6.31779 | -12.336 | 6.0172 | 0.5044 |
| 210 | -5.21813 | -11.6123 | 6.3942 | 0.5360 |
| 215 | -4.03412 | -10.9897 | 6.9556 | 0.5831 |
| 220 | -2.80933 | -10.4181 | 7.6088 | 0.6378 |
| 225 | -2.63924 | -9.86871 | 7.2295 | 0.6060 |
| 230 | -2.46913 | -9.32229 | 6.8532 | 0.5745 |
| 235 | -2.2969 | -8.76524 | 6.4683 | 0.5422 |
| 240 | -2.12389 | -8.1872 | 6.0633 | 0.5083 |
| 245 | -1.94938 | -7.65021 | 5.6308 | 0.4720 |
| 250 | -1.77461 | -6.93844 | 5.1638 | 0.4329 |
| 255 | -1.59884 | -6.25828 | 4.6594 | 0.3906 |
| 260 | -1.42203 | -5.53828 | 4.1163 | 0.3451 |
| 265 | -1.24417 | -4.77862 | 3.5345 | 0.2963 |
| 270 | -1.06527 | -3.97975 | 2.9145 | 0.2443 |
| 275 | -0.88531 | -3.14019 | 2.2549 | 0.1890 |
| 280 | -0.70428 | -2.25467 | 1.5603 | 0.1300 |
| 285 | -0.52218 | -1.43715 | 0.9150 | 0.0767 |
| 290 | -0.33901 | -1.21481 | 0.8758 | 0.0734 |
| 295 | -0.16477 | -0.99472 | 0.8400 | 0.0704 |
| 300 | 0.03054 | -0.77647 | 0.8070 | 0.0676 |

*Molar Composition Error +/- 0.10*

| | |
|---|---|
| Gibbs | 1.55029 |
| x | 14.1850 |
| y | 11.9293 |
| nh | 11.92928 |

TABLE B

MIXED GAS REFRIGERATION METHOD

RELATED APPLICATIONS

This application is a continuation-in-part of prior copending U.S. patent application Ser. No. 08/542,123, filed Oct. 12, 1995, for Miniature Mixed Gas Refrigeration System.

GOVERNMENT LICENSE RIGHTS

The U.S. Government has a paid up license in this invention and the right to have this invention practiced on behalf of the Government, as provided for by the terms of Contract No. CRADA: CN-1090, awarded by the National Institute of Standards and Technology.

FIELD OF INVENTION

This invention is in the field of cooling miniature objects or very small portions of objects to very low temperatures. The objects to be cooled may include biological matter, electronic components, and others.

BACKGROUND OF THE INVENTION

In many different fields of endeavor, it is desirable to be able to selectively cool a very small or even microscopic object to a very low temperature without affecting the temperature of surrounding objects. This is true in the field of electronics, where it may be desirable to apply cooling to a miniature component on a circuit board without substantially cooling adjacent components. It is also true in the field of medicine, where it may be desirable to be able to cool miniature discrete portions of biological tissue to very low temperatures in the performance of cryosurgery, without substantially cooling adjacent tissues of the organ. In the interest of simplicity, this specification will address the fulfillment of this need in the field of medicine, but it should be understood that application of the present invention in other fields, such as electronics, is also contemplated within the scope of the present invention.

Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems are not optimally designed to have sufficient precision and flexibility to allow their widespread use endoscopically and percutaneously.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe or other applicator used in a given application is therefore designed with the optimum shape and size for the application, to achieve this selective freezing of tissue. Where a probe is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe at the location of the tissue to be frozen, without having any undesirable effect on other organs or systems.

Currently known cryosurgical systems typically use liquid nitrogen or nitrous oxide as coolant fluids. Liquid nitrogen is usually either sprayed onto the tissue to be destroyed, or it is circulated to cool a probe which is applied to the tissue. Liquid nitrogen has an extremely low temperature of approximately 77K, and a high cooling capacity, making it very desirable for this purpose. However, liquid nitrogen typically evaporates and escapes to the atmosphere during use, requiring the continual replacement of storage tanks. Further, since the liquid is so cold, the probes and other equipment used for its application require vacuum jackets or other types of insulation. This makes the probes relatively complex, bulky, and rigid, and therefore unsuitable for endoscopic or intravascular use. The need for relatively bulky supply hoses and the progressive cooling of all the related components make the liquid nitrogen instruments less than comfortable for the physician, as well, and they can cause undesired tissue damage.

A nitrous oxide system typically achieves cooling by pressurizing the gas and then expanding it through a Joule-Thomson expansion element, such as a valve, orifice, or other type of flow constriction, at the end of a probe tip. Any such device will be referred to hereinafter simply as a Joule-Thompson "expansion element". The typical nitrous oxide system pressurizes the gas to 700 to 800 psia., to reach practical temperatures of no lower than about 190K to 210K. Nitrous oxide systems are not able to approach the temperature and power achieved by the nitrogen systems. The maximum temperature drop that can be achieved in a nitrous oxide system is to 184K, which is the boiling point of nitrous oxide. The nitrous oxide system does have some advantages, in that the inlet high pressure gas is essentially at room temperature until it reaches the Joule-Thomson element at the probe tip. This eliminates the need for insulation of the system, facilitating miniaturization and flexibility to some extent. However, because of the relatively warm temperatures and low power, tissue destruction and other applications are limited. For many such applications, temperatures below 184K are desirable. Further, the nitrous oxide must typically be vented to atmosphere after passing through the system, since affordable compressors suitable for achieving the high pressures required are not reliable and readily commercially available.

In most Joule-Thomson systems, single non-ideal gasses are pressurized and then expanded through a throttling component or expansion element, to produce isenthalpic cooling. The characteristics of the gas used, such as boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity. Finned tube heat exchangers have been used, but these are necessarily bulky to achieve the required cooling, preventing their use in micro-miniature systems such as catheter delivered instruments. Smaller heat exchangers have also been known, constructed of photo-etched glass plates. These heat exchange systems are still in the range of several centimeters square in size, making them still too bulky for true micro-miniature use, such as in endoscopes, catheters, and other systems. Further, these heat exchangers are planar and difficult to incorporate into tubular structures such as catheters or endoscopes. In many of these medical applications, the dimensions of the components must be less than approximately 3 mm. in width to allow incorporation into through a catheter or endoscope, and preferably less than 15 mm. in length to allow sufficient flexibility.

Heat exchanger requirements can be reduced somewhat by pre-cooling the gases prior to the probe tip heat exchanger. This can be done by incorporating a Peltier device in the flow path prior to the probe tip heat exchanger. Gas flowing through a heat exchanger on the surface of the cold side of the Peltier device would be cooled prior to reaching the probe tip heat exchanger. Alternatively, the inlet high pressure stream could be split so that a portion of the stream could be diverted and expanded to cool the remaining portion of the inlet stream prior to reaching the probe tip heat exchanger.

A dramatic improvement in cooling in Joule-Thomson systems can be realized by using a mixture of gasses rather than a single gas. For example, the addition of hydrocarbons to nitrogen can increase the cooling power and temperature drop for a given inlet pressure. Further, it is possible to reduce the pressure and attain performance comparable to the single gas system at high pressure. Similar to single gas systems, these mixed gas systems have heat exchanger requirements and are limited in their miniaturization potential by the size of the heat exchanger. The improvement in cooling performance realized by mixed gas systems is very desirable for medical and other microminiature systems.

Some mixed gas systems have been designed where high pressure is not a major concern, and where bulky high efficiency heat exchangers can be used, but they are typically used in defense and aerospace applications. The glass plate heat exchangers mentioned above are used in some such systems, and these systems sometimes require pressures of 1200 psia. In many applications, such as laser systems, superconductors, electronics and cryosurgery, pressures above approximately 420 psia. are undesirable for safety reasons, and because the devices exhibit poor longevity, high cost, and poor reliability. Further, endoscopic or percutaneous use prevents implementation of any heat exchanger having a width of greater than about 3 mm. or a length of more than about 15 mm.

Specifically, it would be desirable to develop a long, slender, flexible cryoprobe, such as a transvascular cardiac catheter. Cardiac catheters must be very slender, in the range of less than 5 mm., and they must exhibit considerable flexibility, in order to be inserted from an access point in a remote blood vessel into the heart. A cryosurgical catheter to be used in such an application must also have a relatively low operating pressure for safety reasons. It must have the cooling capacity to overcome the ambient heat load imposed by the circulating blood, yet it must be able to achieve a sufficiently low temperature to destroy the target tissue. Finally, the cold heat transfer element must be limited to the tip or end region of the catheter, in order to prevent the damaging of tissue other than the target tissue.

It is an object of the present invention to provide a method of formulating an optimum fluid mixture and using the fluid mixture in a miniature mixed gas refrigeration system which is capable of achieving a cooling temperature of 183K or less, utilizing a high pressure of no greater than 420 psia., with components capable of fitting within a miniature delivery system such as a transvascular cardiac catheter. It is a further object of the present invention to provide a method of formulating an optimum fluid mixture and using the fluid mixture in a miniature refrigeration system utilizing a microminiature heat exchanger to provide a sufficiently cool high pressure gas mixture for isenthalpic expansion through a Joule-Thomson expansion element, to achieve an expanded gas temperature of at least as low as 183K, to have sufficient cooling power to maintain this temperature when a heat load is applied, and to perform with an inlet high pressure of no greater than 420 psia.

SUMMARY OF THE INVENTION

The present invention comprises a method of operating a miniature refrigeration system, including a method for selecting an optimum fluid mixture for use as the cooling medium. The term "gas mixture" will be used to some extent in the present application, but it should be understood that this term is not intended to be limited to mixtures having no liquid components, in view of the well known fact that most compositions commonly referred to as gases actually have some liquid content at some temperatures and pressures. The refrigeration system has a compressor for compressing a gas mixture to a pressure up to 420 psia. The high pressure gas mixture from the compressor is fed into a high pressure supply tube, such as in inner tube of a cardiac catheter, which in turn feeds the high pressure gas mixture into the inlet port at the proximal end of a cylindrical microminiature counterflow heat exchanger. The high pressure gas mixture passes through a high pressure supply passageway within the heat exchanger and exits through a port at the distal end of the heat exchanger. The high pressure distal port is connected to the inlet of a Joule-Thomson expansion element, in which the gas mixture is isenthalpically expanded to a lower pressure and a temperature at least as low as 183K. The expansion element can have a second stage in which the gas mixture is further expanded isothermally to absorb additional heat from the surroundings.

The gas mixture escaping from the Joule-Thomson expansion element is exposed to the inner surface of a heat transfer element mounted in the wall of an outer tube coaxial with the inner tube. The expanded gas mixture cools the heat transfer element to a temperature of at least as low as 183K and then returns through the low pressure return passageway of the heat exchanger. This cools the high pressure gas from its original ambient temperature to a lower temperature. From the low pressure outlet of the heat exchanger, the expanded gas mixture flows into the lumen of the outer tube, outside the inner high pressure tube, to return to the compressor.

The heat exchanger can have a laminated construction of several different types. In a preferred embodiment, the heat exchanger is constructed of a plurality of plates and spacers stacked alternatingly along the axial dimension of the heat exchanger. The plates have a first plurality of holes establishing the high pressure passageway of the heat exchanger, and a second plurality of holes establishing the low pressure passageway of the heat exchanger. The high pressure holes are segregated from the low pressure holes. Spacers with larger openings are stacked between the plates to promote turbulent flow and insure effective heat exchange. The plates and spacers can be fastened together by a process such as diffusion bonding.

The Joule-Thomson expansion element can be a sintered metal plug made by sintering a plurality of metal beads into a metal cup, to provide the required pressure drop. The two different stages, if present, can utilize different sizes of beads, different cross sectional areas, and different packing densities. The heat transfer element can take the optimum shape for matching the object or tissue to be cooled. For example, a metal plug can be installed in the tip of the outer tube or catheter, for applying cooling through the extreme distal tip of the catheter. Alternatively, a relatively narrow metal strip can be mounted in a side wall of the catheter, near the distal tip, for applying cooling to a narrow strip of tissue.

The method of operating the apparatus described above includes the selection of an optimum gas mixture for use as the cooling medium. In the miniature environments envisioned for the use of this apparatus, severe size limitations will be placed upon the heat exchanger used. For instance, a cardiac catheter necessarily is severely limited in diameter by the diameter of the blood vessels through which the catheter must pass. Further, maneuverability requirements dictate that the catheter be somewhat flexible, and the heat exchanger will probably be somewhat stiff, if not rigid. Therefore, the allowable length of the heat exchanger is severely limited. Limitation of the size of the heat exchanger naturally limits the amount of heat which can be transferred in the heat exchanger.

This type of severe limitation on the size and capacity of the heat exchanger dictates that the system be optimized by selection of a gas mixture which will have the appropriate thermodynamic properties to perform as well as possible. The goal of this selection process is to maximize the cooling power of the combination of the pre-cooling heat exchanger and the Joule-Thomson expansion element. For a given gas mixture operating between selected high and low pressures and between selected high and low temperatures, there is a limit to the amount of heat which can be transferred, even in a perfect heat exchanger. The present invention includes a method for selecting, from among a group of gas mixture candidates, a mixture which will maximize the performance ratio between the refrigeration power of the Joule-Thomson expansion element and the heat transfer capacity of a perfect heat exchanger.

The method involves first compiling a list of component fluids, which will be combined in various mixtures to arrive at an optimum mixture. It is necessary for each fluid mixture to have a triple point below the lowest temperature to be encountered, to ensure that the fluid mixture can not possibly freeze in the apparatus. Various methods could be employed to insure that each fluid mixture possesses this quality. One method is to insure that each of the component fluids has a triple point below the lowest temperature to be encountered. This would ensure that any mixture of those fluids would meet this criterion. It is common, however, for a fluid mixture to have a triple point below the triple points of several of its components. Therefore, it would be feasible to use several component fluids having triple points above the lowest temperature to be encountered, as long as the triple point of each fluid mixture is computed to be below the lowest temperature to be encountered.

It is also necessary for the fluid mixture to possess a positive Joule-Thomson coefficient, to ensure that a drop in pressure is accompanied by a drop in temperature. As with the triple point criterion, this can be accomplished by ensuring that each component fluid has a positive Joule-Thomson coefficient. However, it is also possible for a fluid mixture to have a positive Joule-Thomson coefficient, even though several of its component fluids have negative coefficients. Therefore, it would be feasible to use several component fluids having negative coefficients, as long as the coefficient of each fluid mixture is computed to be a positive value.

For each of the component fluids in this list, the molar enthalpy is known at a plurality of data points over a selected range of temperatures and a selected range of pressures, with these ranges including the temperatures and pressures at which the fluid mixture will be pumped through the apparatus. Then, various mixtures of the fluids are selected, with each mixture having up to a selected maximum number of component fluids. Based upon the known thermodynamic properties of the component fluids, the molar enthalpy of each fluid mixture is then calculated at a plurality of data points over the selected range of temperatures and the selected range of pressures.

For each fluid mixture, a series of calculations are then performed. It can be assumed that the pressure drop through the heat exchanger, on either the high pressure side or the low pressure side, is negligible. Alternatively, a starting pressure can be chosen which takes into account the anticipated pressure drop in the heat exchanger. For the low pressure in the selected pressure range, the molar enthalpy of the fluid mixture at the low temperature in the selected temperature range is subtracted from the molar enthalpy at the high temperature in the range, yielding a low pressure enthalpy difference between the fluid mixture states at the two temperatures. Similarly, for the high pressure in the selected pressure range, the molar enthalpy at the low temperature is subtracted from the molar enthalpy at the high temperature, yielding a high pressure enthalpy difference between the fluid mixture states at the two temperatures. The lesser of these two enthalpy differences is the maximum molar enthalpy difference which could be achieved in a perfect counterflow heat exchanger operating with the selected fluid mixture over the selected temperature range and pressure range. The maximum possible heat transfer capacity of such a heat exchanger with the selected fluid mixture is the product of the molar flow rate of the fluid mixture and this molar enthalpy difference.

Then, for each selected fluid mixture, at a plurality of selected temperatures over the selected temperature range, the molar enthalpy of the fluid mixture at the high pressure in the selected pressure range is subtracted from the molar enthalpy at the low pressure in the range, yielding a molar enthalpy difference between the fluid mixture states at the two pressures, for each of the plurality of temperatures. The plurality of temperatures at which this calculation is performed are selected at uniform intervals over the selected temperature range. As an example, if the selected temperature range is from 120K to 270K, the intervals between the selected plurality of temperatures might be set at five degree increments, for a total of 30 intervals, and 31 selected temperatures. This calculation is then performed at each of the 31 temperatures. The higher the number of selected temperatures used, the greater will be the usefulness of the information calculated. The molar enthalpy difference calculated at each of these selected temperatures is the enthalpy increase which would occur during expansion of the selected fluid mixture from the high pressure to the low pressure, if the temperature were to remain constant.

In Joule-Thomson expansion, there is very little or no opportunity for heat transfer to or from the fluid as it flows through the expansion element, no change in potential energy of the fluid, no work performed, and very little or no change in kinetic energy of the fluid. Therefore, the enthalpy states of the fluid before and after the expansion are essentially the same. As the pressure sharply decreases, the temperature of the fluid also sharply decreases, maintaining an essentially constant enthalpy. This colder fluid then can be used to cool the surroundings. The maximum possible refrigeration power available through Joule-Thomson expansion over the selected pressure range, with the selected fluid mixture, is the product of the molar flow rate of the fluid mixture and the lowest molar enthalpy difference calculated at any temperature over the selected temperature range.

Therefore, each fluid mixture in the group exhibits a maximum possible refrigeration power and a maximum possible heat transfer capacity. In order to optimize the operation of the apparatus of the present invention, a fluid mixture is chosen from among the candidates described above, which will result in the highest performance ratio between the available refrigeration power and the available heat transfer across a heat exchanger. That is the optimum fluid mixture within the temperature and pressure ranges selected. It can be seen that, if the performance ratio is equal to or greater than unity, meaning that the available refrigeration power is as great as the available heat transfer, then the maximum cooling possible over the desired temperature and pressure range can be achieved through Joule-Thomson expansion alone, and no heat exchanger is needed. If the highest performance ratio is less than unity, a heat exchanger will be required.

The novel features of this invention, as well as the invention itself, will be best understood from the attached drawings, taken along with the following description, in which similar reference characters refer to similar parts, and in which:

BRIEF DESCRIPTION OF THE DRAWINGS

FIGS. 16 through 32 show enthalpy tables and graphs for seventeen fluid mixtures, for exemplary purposes.

DESCRIPTION OF PREFERRED EMBODIMENTS

Figure 1:
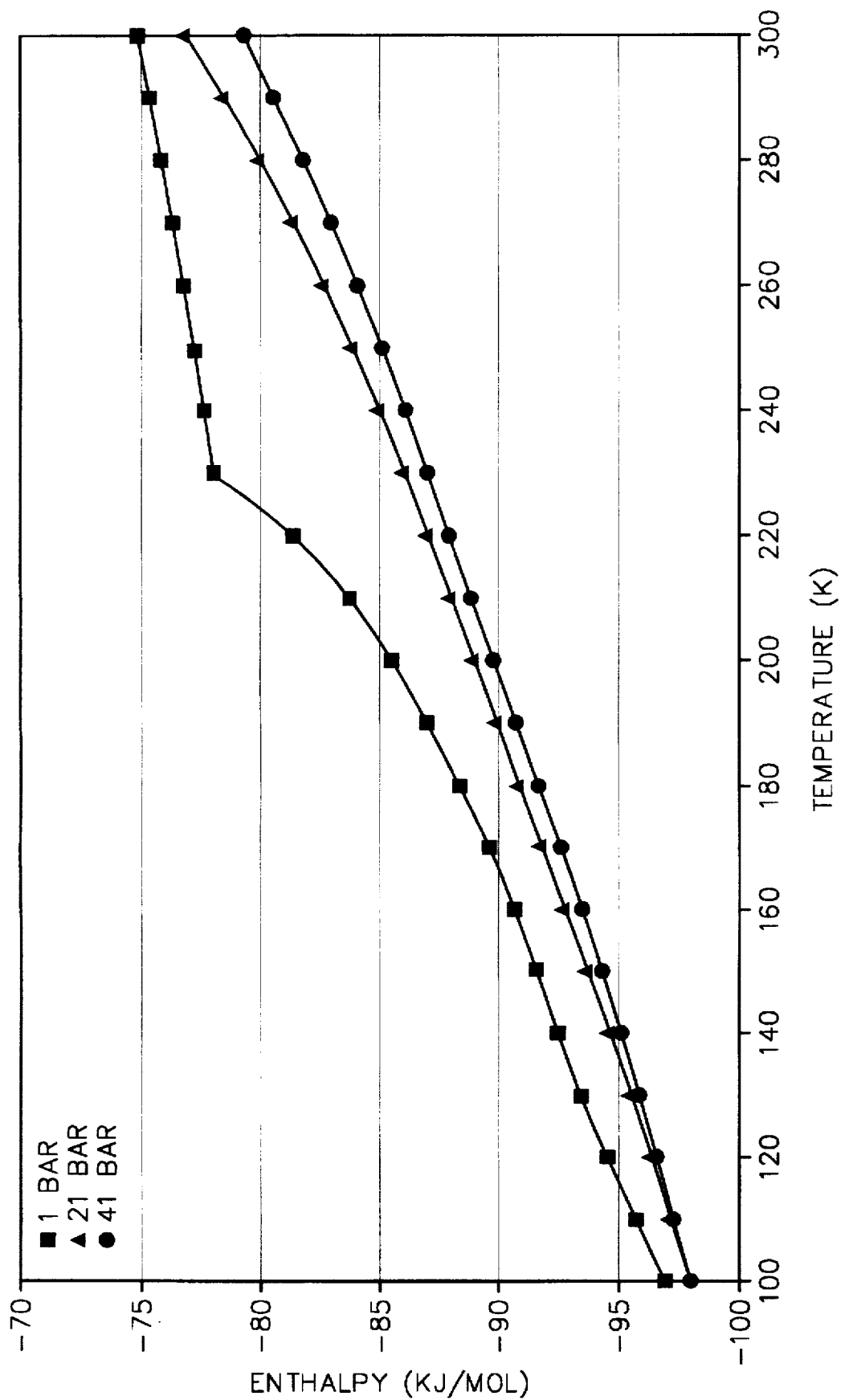
FIG. 1 is a graph of enthalpy vs. temperature for a typical gas mixture used with the present invention.

A key to the success of the present invention lies in the selection of an optimum fluid mixture, since no known single gasses are capable of achieving the necessary cooling capacity at the required temperatures, given the size limitations and pressure limitations imposed on systems intended for use in the selected applications. Several gas mixtures have been identified for use with the present invention, and it is anticipated that others will be identified as well. Appropriate gas mixtures may take various forms, and they may be either hydrocarbon-based or non-hydrocarbon-based. Some fluid mixtures function significantly better than other mixtures, so it is important to be able to identify and select an optimum mixture from among a group of available mixtures. One mixture currently identified as useful for many applications is 30 percent Methane, 23 percent Nitrogen, 23 percent Isobutane, 19 percent Ethane, and 5 percent Propane. The temperature capability of isenthalpic expansion of such a gas mixture is illustrated by FIG. 1, which shows enthalpy curves for this gas mixture at pressures of 1 bar (14.5 psia.), 21 bar (305 psia.), and 41 bar (595 psia.). Isenthalpic expansion from one of the higher pressures to the lower pressure proceeds horizontally to the left across the graph, accompanied by a drop in temperature. The lowest temperature attainable would be at the point where the curves cross, somewhere below 100K. The lower the temperature of the high pressure gas mixture, the lower the temperature which can be achieved by the isenthalpic expansion through the Joule-Thomson expansion element. It can also be seen from the graph that there is little difference between the temperatures attainable by expanding from 41 bar and expanding from 21 bar. For example, assume that the heat exchanger used is capable of cooling the high pressure gas mixture to a temperature of 210K, just upstream of the expansion element. If a high pressure of 21 bar is used, the isenthalpic expansion will result in a temperature of 180K. If the gas mixture is instead pressurized to 41 bar, the attainable temperature after isenthalpic expansion is still only about 173K. Further, the cooling capacity, or power, represented by the difference between the high pressure curve and the 1 bar curve at a given temperature is similar, whether the high pressure is 21 bar or 41 bar. Therefore, the added safety achieved by lowering the initial pressure to 21 bar, or approximately 300 psia, results in only a minor loss of performance. Obviously, for a given gas mixture, the more efficient the heat exchanger, the lower the probe temperature that can ultimately be obtained, and the greater will be the cooling power.

Figure 2:
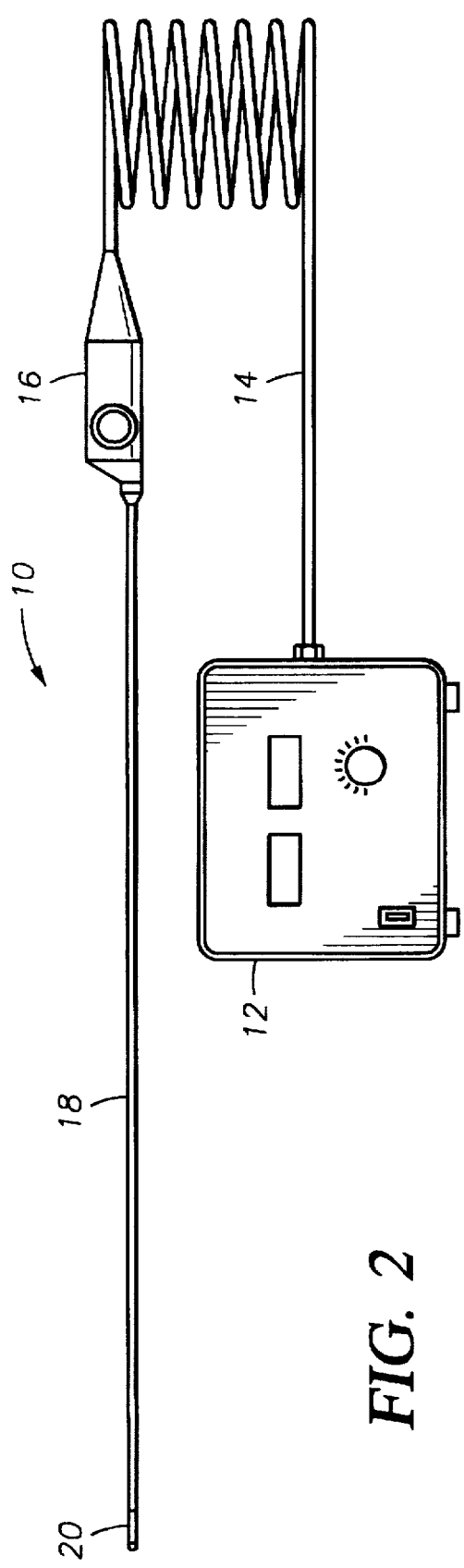
FIG. 2 is a perspective view of one embodiment of the miniature refrigeration system of the present invention.

FIG. 2 shows a refrigeration system 10 according to the present invention, for a cryosurgical application. The system 10 consists of a commercially available single stage compressor 12, a flexible dual lumen hose 14 connected to the inlet and outlet of the compressor 12, a steering handle 16, and a cryosurgical probe 18. The compressor 12 can be any of several compressors available, often using an aftercooler, an oil separator, and an adsorption filter. Alternatively, an oil free compressor could also be utilized. The hose 14 can be any flexible dual lumen hose suitable for the pressures and chemical exposures involved, for the gas mixture used. The handle 16 can have a control expansion element installed, for the physician to use in throttling the flow rate of the gas mixture. Alternatively, the flow could be controlled via a foot switch that regulates flow at the compressor. The probe 18 is a coaxial catheter having an inner tube for conducting the high pressure gas mixture from the outlet of the compressor 12 and for returning the expanded low pressure gas to the inlet of the compressor 12. The probe 18 has a distal end portion or region 20 in which the heat exchanger, expansion element, and heat transfer element are located. The probe 18 is of suitable diameter, length, and flexibility to be inserted to the object to be cooled, such as through the vascular system of a patient into the heart.

Figure 3:
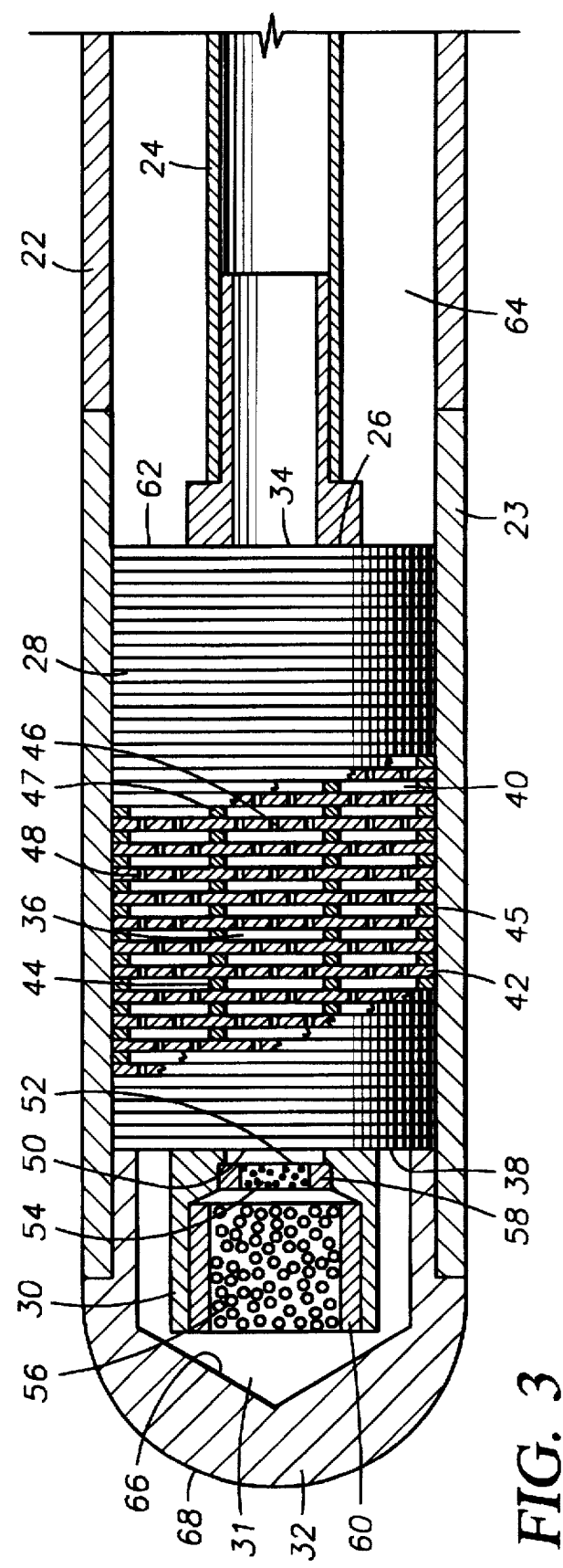
FIG. 3 is a partial section view of the distal end portion of the cryosurgical probe portion of the refrigeration system shown in FIG. 2.

FIG. 3 shows a partial section view of the distal end portion 20 of the coaxial catheter 18. The catheter 18 consists of an outer tube 22 and an inner tube 24. The outer tube 22 can be continuous to the end of the catheter 18, or it can have an extension 23, which should be considered for all practical purposes an integral part of the outer tube 22. The outer tube 22 is made according to known methods from a wire-braided polymer, such as a polyamide-ether copolymer. The inner tube 24 is made from a wire-braided polyimide having a pressure capability sufficient for the maximum high pressure anticipated for the particular application. The inner tube 24 is connected by means of an inlet fitting 26 to the proximal end of a micro-miniature heat exchanger 28. Mounted to the distal end of the heat exchanger 28 is a Joule-Thomson expansion element 30. The distal end of the expansion element 30 is exposed to a cavity 31 at the distal end of the outer tube 22 or extension 23, closed by a heat transfer element 32. The expanded gas mixture cools the inner surface 66 of the heat transfer element 32, thereby cooling the outer surface 68. The outer surface 68 is placed against the object to be cooled by the physician.

More specifically, the distal end of the inner high pressure tube 24 is connected by means of the inlet fitting 26 to the high pressure inlet port 34 at the proximal end of the heat exchanger 28. This high pressure inlet port 34 leads to a high pressure supply passageway 36 through the heat exchanger, shown as the central axial portion of the heat exchanger 28 in this embodiment. The heat exchanger 28 also has a low pressure inlet port 38 at its distal end exposed to the cavity 31. This low pressure inlet port 38 leads to a low pressure return passageway 40, shown as the outer annular portion of the heat exchanger, surrounding the high pressure passageway 36. The low pressure, low temperature gas mixture flowing through the low pressure passageway pre-cools the high pressure, higher temperature gas mixture flowing through the high pressure passageway. The heat exchanger 28 is constructed of alternately stacked copper plates 42 and stainless steel spacers 44, diffusion bonded together. Other methods of attachment could be used without departing from the spirit of the present invention. The heat exchanger 28 is shown, for the sake of simplicity in this figure, as having an outer skin over the plates 42 and spacers 44, but in actuality, the skin is optimally provided by an outer ring 45 on each spacer 44 being bonded to the extreme outer annular portion of each plate 42, as will be made more clear below. The central portion of each plate 42 has a plurality of holes 46 therethrough, which along with central openings in the spacers 44 establish the high pressure passageway 36 longitudinally through the heat exchanger 28 in the distal direction. Similarly, the outer portion of each plate 42 has a plurality of holes 48 therethrough, which along with outer openings in the spacers 44 establish the low pressure passageway 40 longitudinally through the heat exchanger 28 in the proximal direction. The high pressure passageway 36 is separated from the low pressure passageway 40 by an inner ring 47 on each spacer 44.

High pressure gas mixture passing through the heat exchanger 28 exits the high pressure passageway at a high pressure outlet port 50 at the central distal portion of the heat exchanger to enter the inlet 52 of the Joule-Thomson isenthalpic expansion element 30. This expansion element 30 has a first stage 54 of a first diameter, in which isenthalpic expansion to a second larger diameter takes place, lowering the temperature of the gas mixture to the design temperature. The gas mixture then passes through the second stage 56 in which isothermal expansion takes place, leaving the gas mixture still at the desired temperature, but absorbing heat from the surrounding structure in the process. The first stage 54 is constructed by filling a metal cylinder 58 with a selected size of metal beads, at a selected packing density, to achieve the desired rate of expansion of the gas. The beads are sintered in place in the cylinder 58. Similarly, the second stage 56 is constructed by filling a second metal cylinder 60 with a selected size of metal beads, at a selected packing density, to achieve the desired rate of expansion of the gas. Typically, the beads in the second stage 56 will have a larger surface area to enhance heat transfer.

The expanded gas mixture which passes through the heat exchanger 28 in the proximal direction exits the annular low pressure passageway 40 at a low pressure outlet port 62 at the proximal end of the heat exchanger 28. This expanded gas mixture enters the inner lumen 64 of the outer tube 22, surrounding the inner tube 24, to be returned to the compressor 12.

Figure 5:
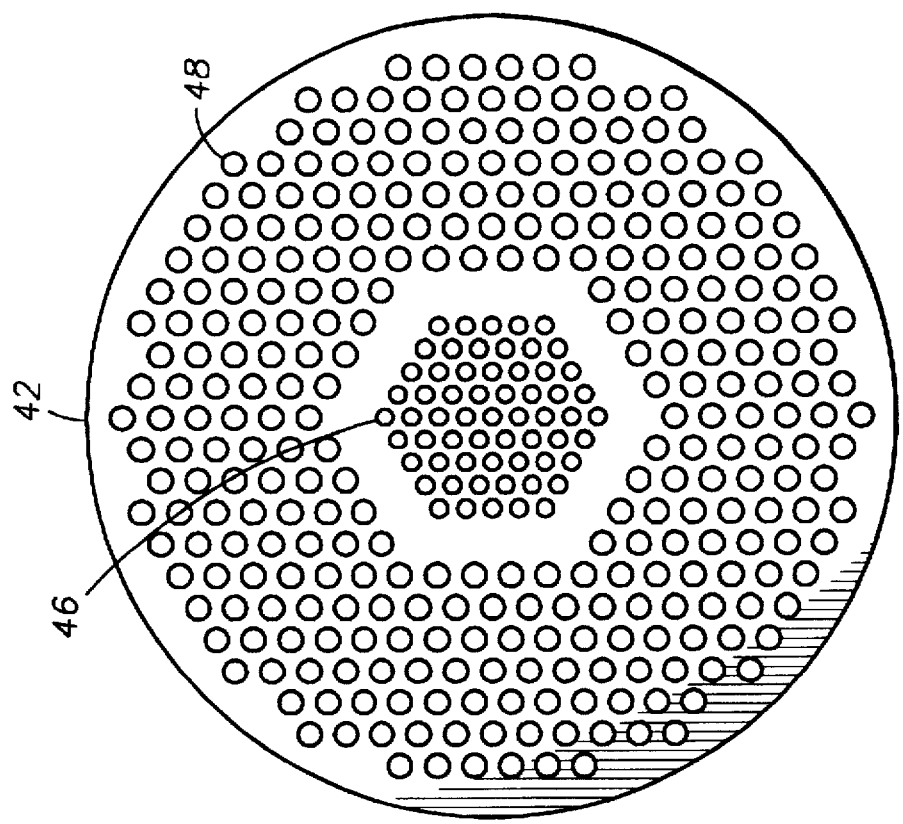
FIG. 5 is an elevation view of a second configuration of heat exchanger plate, showing a different angular orientation of holes from the orientation shown in FIG. 4.
Figure 4:
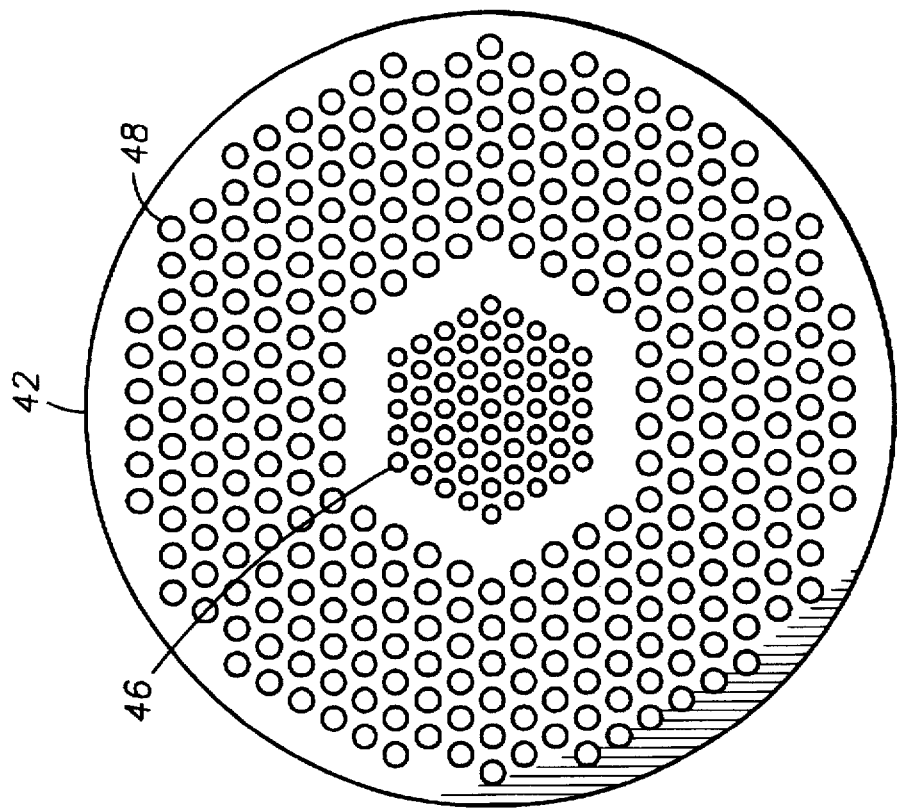
FIG. 4 is an elevation view of a preferred embodiment of one configuration of heat exchanger plate used in the micro-miniature heat exchanger utilized in the cryosurgical probe shown in FIG. 3.

FIGS. 4 and 5 more clearly illustrate the structure of the plates 42 and their angular orientation within the heat exchanger 28. Each plate 42 has a first plurality of high pressure holes 46 through its central portion, and a second plurality of low pressure holes 48 through its outer annular portion. Typically, the diameter and spacing of the inner holes 46 are smaller than the diameter and spacing of the outer holes 48. Selection of hole diameter and spacing for the two different passageways is designed for an optimization of minimum pressure drop and maximum heat transfer rate at the two different pressures, according to well known design principles. FIGS. 4 and 5 are also intended to show the relative angular orientation between adjacent plates 42. It can be seen that the two figures actually depict the same plate configuration, with the plate 42 in FIG. 5 simply being rotated relative to the plate 42 in FIG. 4. The hole pattern used in the plate 42 can be varied, with the objective being to maximize the heat exchange contact between the gas mixture and the plate 42. Gas does not flow from the high pressure portion of the plate to the low pressure portion, being prevented by contact between the plate 42 and the inner ring 47 of the interdisposed spacer 44, as shown earlier in FIG. 3. The relative angular orientation between adjacent plates 42 can also be varied according to the chosen hole pattern, with the objective being to maximize turbulence of the gas mixture, to promote heat transfer. It can be clearly seen from FIGS. 3, 4, and 5 that gas flowing through the heat exchanger 28 in either of the passageways 36, 40 follows a somewhat tortuous path, with a substantial portion of the flow path being involved in movement transverse to the axis of the heat exchanger 28. In the embodiment shown, the transverse component of the flow results from the relative angular orientation between adjacent plates 42. This tortuous path promotes efficient heat transfer, allowing the micro-miniature heat exchanger 28 to achieve the required temperature drop to enable the desired isenthalpic expansion through the Joule-Thomson flow restriction expansion element 30, ultimately producing the designed cooling temperature. Heat flow in this embodiment tends to be substantially radial.

Figure 6:
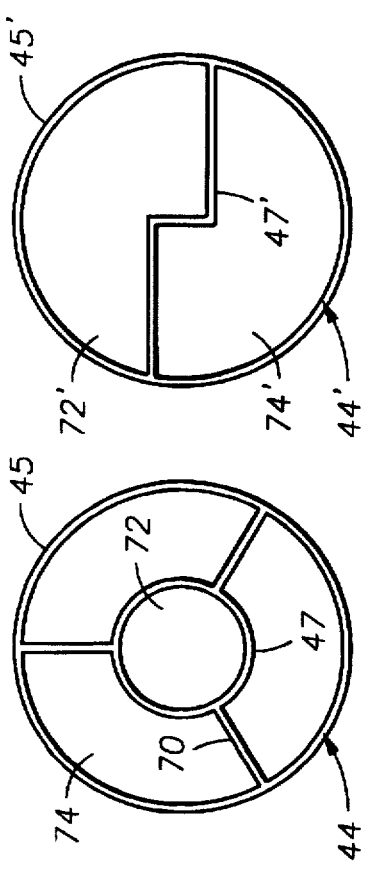
FIG. 6 is an elevation view of a preferred embodiment of a spacer used in the micro-miniature heat exchanger used in the probe shown in FIG. 3.

FIG. 6 shows the preferred embodiment of the spacer 44, which is interspersed between the plates 42. The spacer 44 has an outer ring 45 and an inner ring 47 supported in the desired concentric relationship by spokes 70. An inner opening 72 within the inner ring 47 serves as a portion of the high pressure passageway 36 between plates 42. A plurality of outer openings 74 between the inner ring 47 and the outer ring 45 serve as a portion of the low pressure passageway 40 between plates 42. The inner ring 47 serves as a divider between the high and low pressure openings 72, 74.

Figure 8:
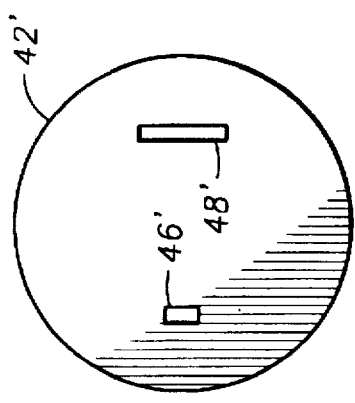
FIG. 8 is an elevation view of a first configuration of plate used in the second embodiment of the micro-miniature heat exchanger.
Figure 7:
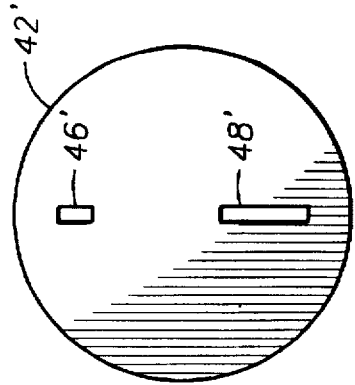
FIG. 7 is an elevation view of a second embodiment of a spacer used in a second embodiment of the micro-miniature heat exchanger.
Figure 9:
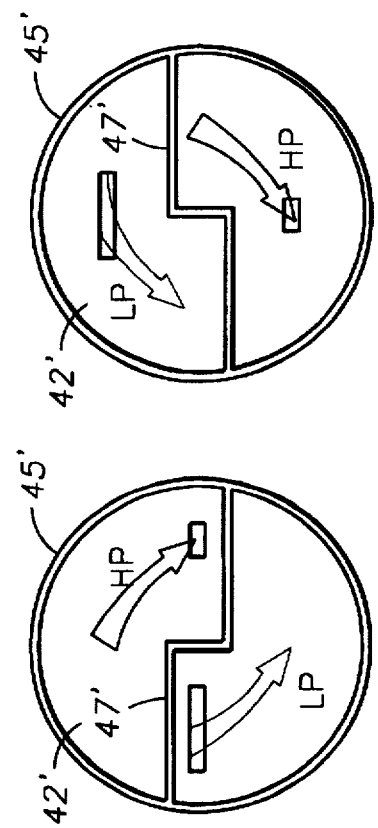
FIG. 9 is an elevation view of a second configuration of plate used in the second embodiment of the micro-miniature heat exchanger, showing the different orientation of high pressure and low pressure ports.

FIG. 7 shows a second embodiment of the spacer 44' which can be used with a second embodiment of plates 42' shown in FIGS. 8 and 9. The spacer 44' has an outer ring 45' and a high/low pressure divider 47'. This divider 47' separates the high pressure opening 72' from the low pressure opening 74'. It can be seen that this spacer 44' can be turned over from the orientation shown in FIG. 7, to reverse the orientation of the divider 47', for reasons that will become apparent below. FIG. 8 shows a plate 42' having a relatively small rectangular high pressure hole 46' and a relatively large rectangular low pressure hole 48', with the long dimensions of the rectangular holes 46', 48' being vertically aligned. FIG. 9 shows the same type of plate 42', with the rectangular holes 46', 48' being arranged horizontally. These two hole patterns and the two spacer orientations possible with the spacer 44' are used to create a series of adjacent plates 42' and spacers 44' as shown in FIG. 10.

Figure 10:
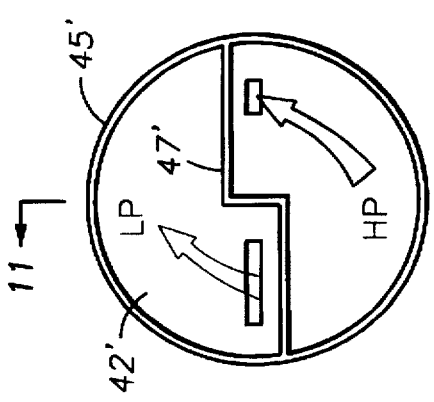
FIG. 10 is a series of elevation views of plates and spacers used in the second embodiment of the micro-miniature heat exchanger, showing the flow of supply and return gas mixtures.
Figure 11:
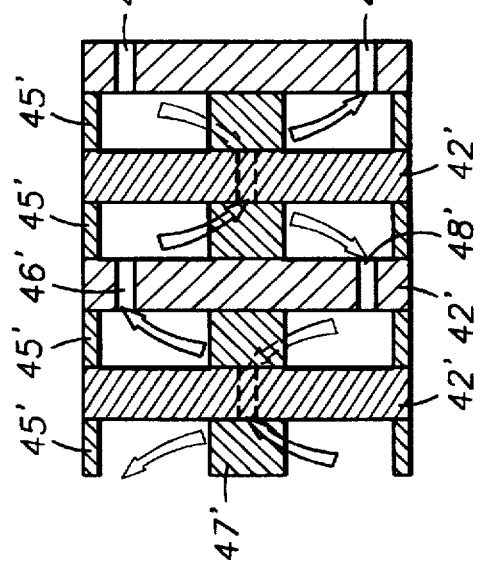
FIG. 11 is a sectional view of the plurality of plates and spacers shown in FIG. 10, showing the flow of supply and return gas mixtures.

FIG. 10 shows this series arranged from left to right as they would be arranged from the proximal end of the heat exchanger toward the low pressure end, in successive series. The HP arrows show the flow path of the high pressure gas mixture into the plane of the page, while the LP arrows show the path of the low pressure gas mixture out of the plane of the page. FIG. 11 further illustrates this flow path, by showing a vertical section through the stacked plates 42' and spacers 44'. Dashed lines are used to show the locations of hidden high and low pressure holes. Here again, it can be seen that the gas mixture follows a tortuous path through both the high pressure and low pressure passageways 36, 40, but in this embodiment, the transverse components of the flow are much more pronounced than in the first embodiment, and the heat flow tends to be more axial than radial.

Figure 12:
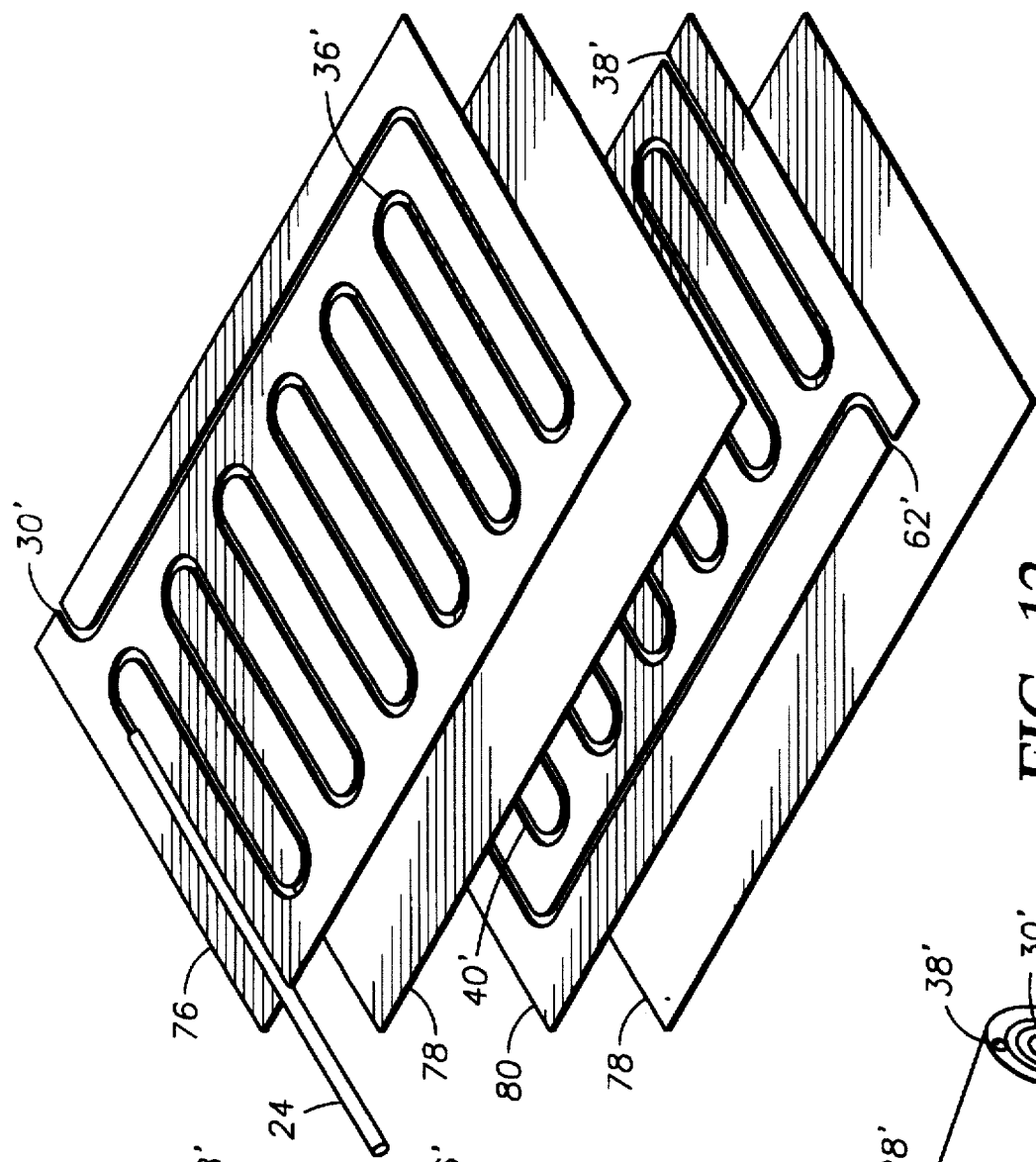
FIG. 12 is a perspective view of a third embodiment of the micro-miniature heat exchanger used in the present invention, prior to final shaping.
Figure 13:
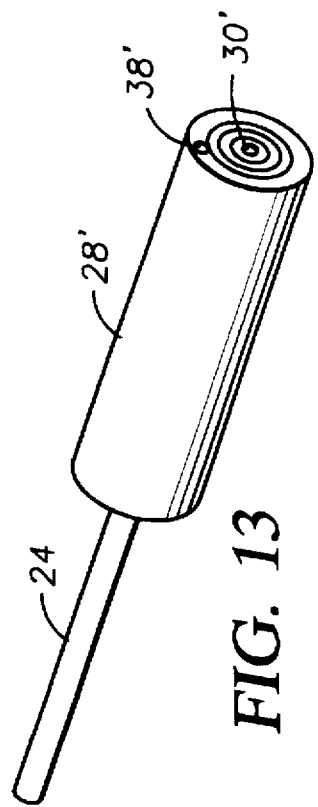
FIG. 13 is a perspective view of the heat exchanger shown in FIG. 12, after final shaping.

FIGS. 12 and 13 show yet another embodiment of the heat exchanger of the present invention, constructed of rolled sheets, rather than stacked plates and spacers. The inner tube 24 of the catheter 18 is shown connected to a labyrinthian high pressure passageway 36' etched into a first sheet 76. A constriction is also etched into the outlet of the high pressure passageway 36', to form a Joule-Thomson expansion element 30'. A second sheet 80 has a low pressure passageway 40' etched therein, with an inlet 38' and an outlet 62'. Positioned in between the first sheet 76 and the second sheet 80 are spacer sheets 78 to separate the high pressure and low pressure passageways 36', 40'. The sheets 76, 78, 80 can be laminated in the orientation shown and diffusion bonded together, or joined by some other suitable process. The assembly is then rolled as shown in FIG. 13, to construct a cylindrical heat exchanger 28'.

Figure 14:
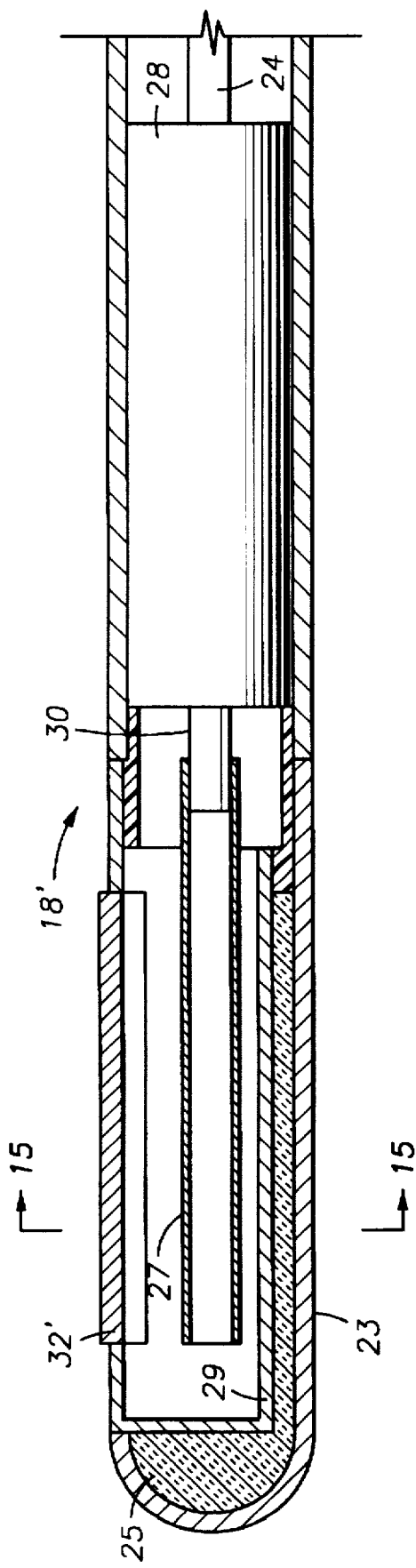
FIG. 14 is a partial section view of a second embodiment of the distal end portion of the cryosurgical probe used in the present invention, showing a narrow elongated heat transfer element.
Figure 15:
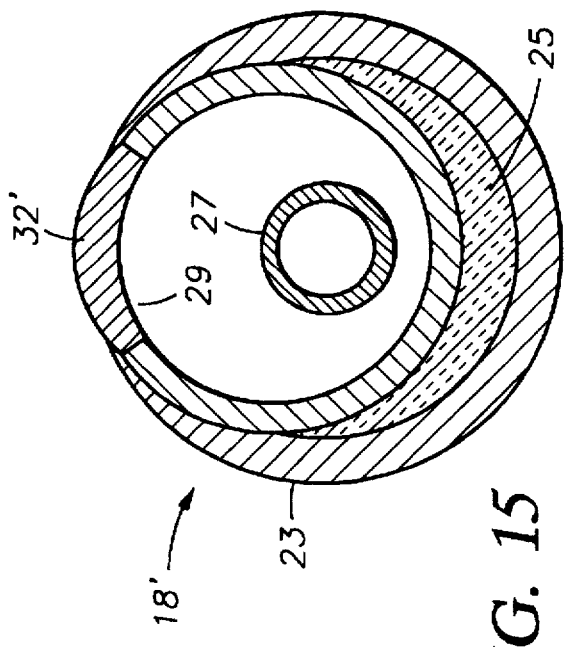
FIG. 15 is a section view of the second embodiment, taken along the line 15—15 in FIG. 14.
Figure 16:
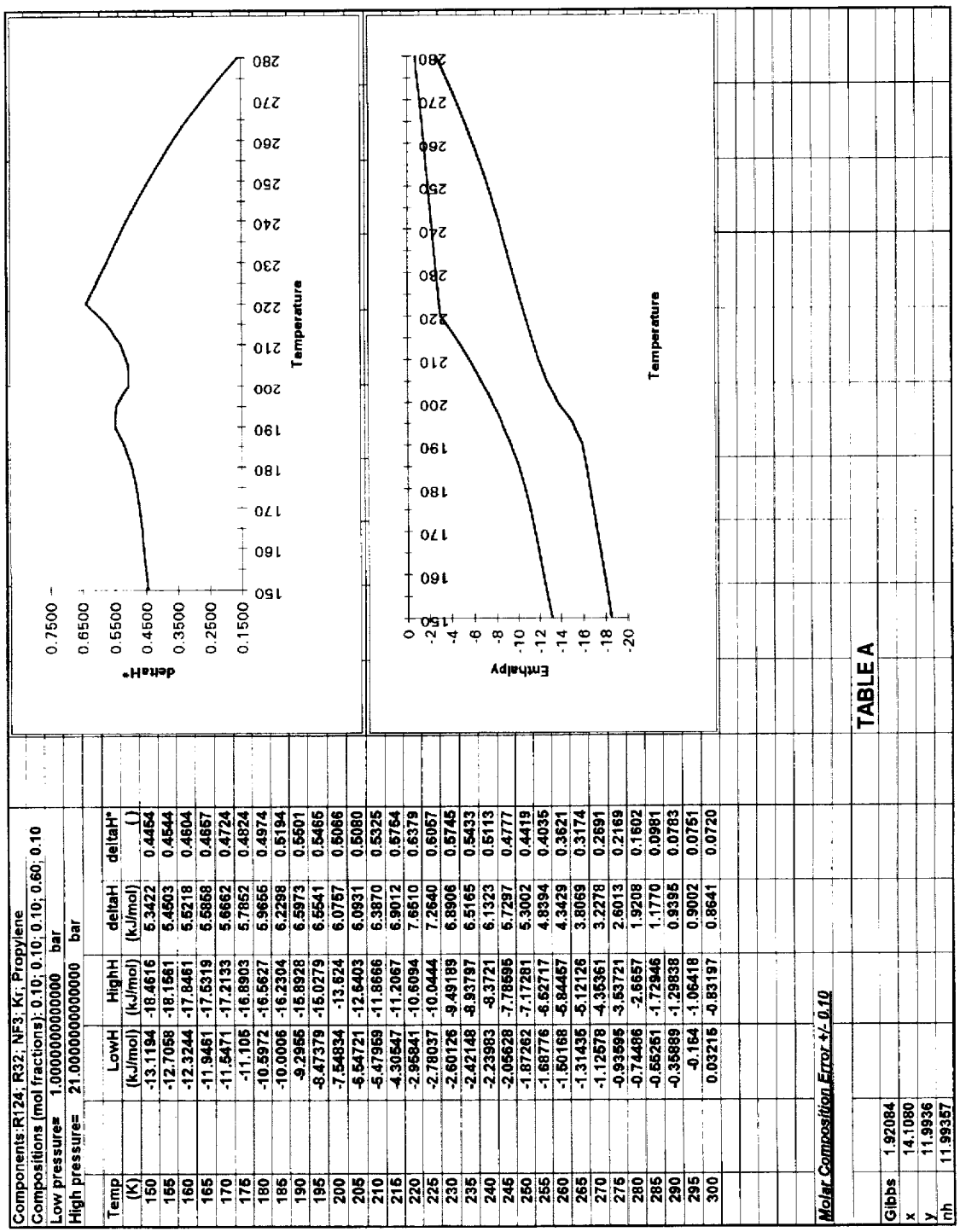
Figure 18:
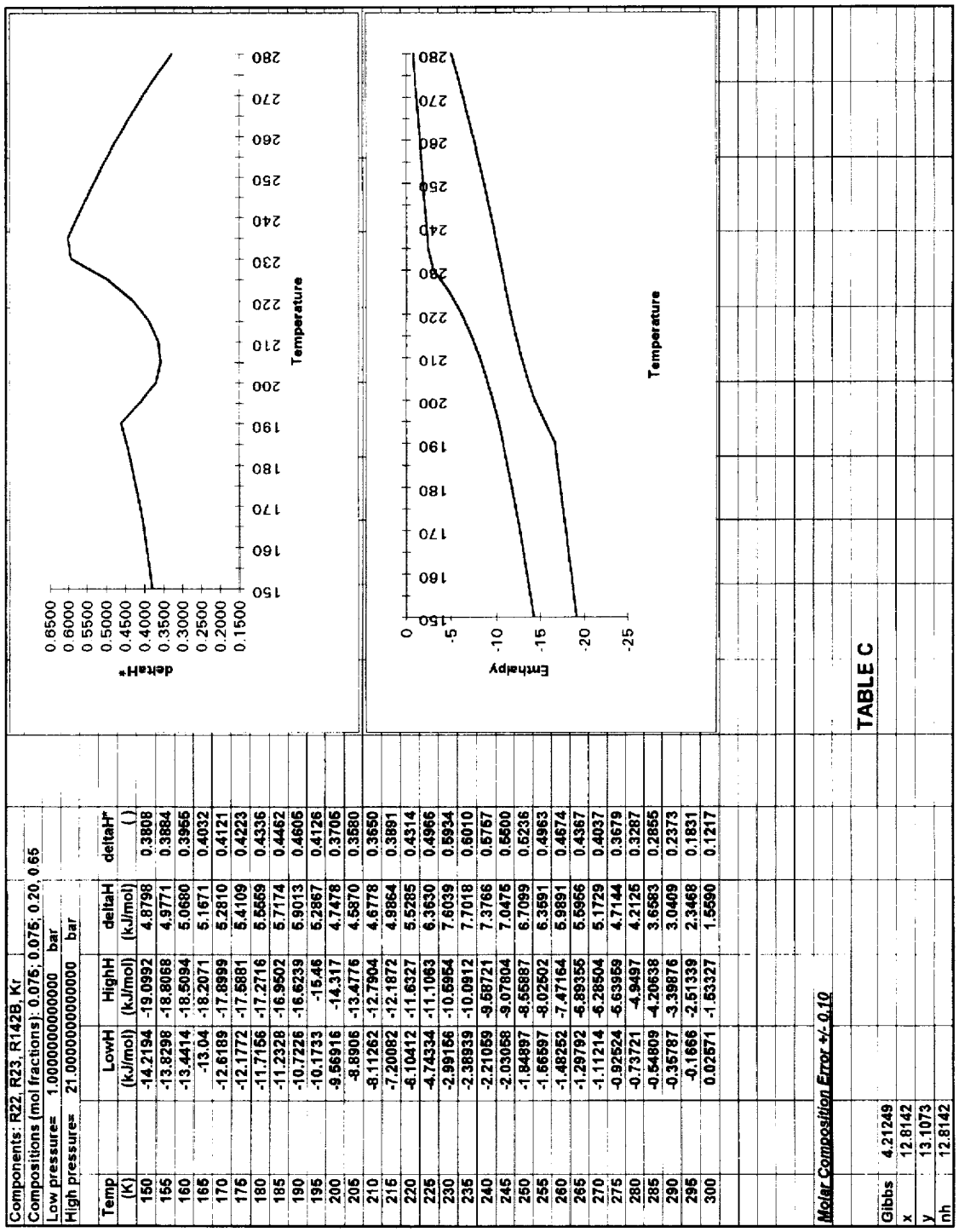
Figure 19:
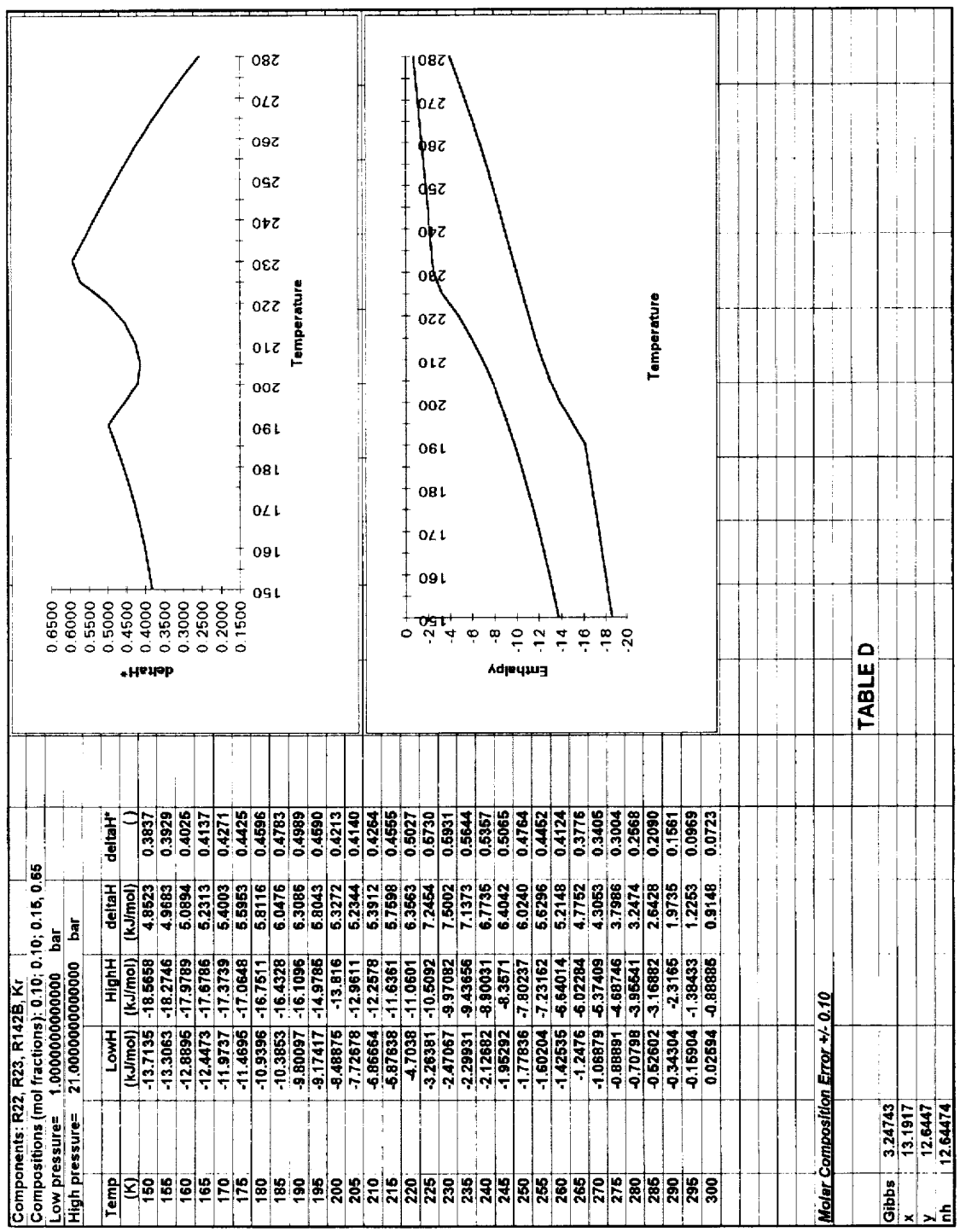
Figure 20:
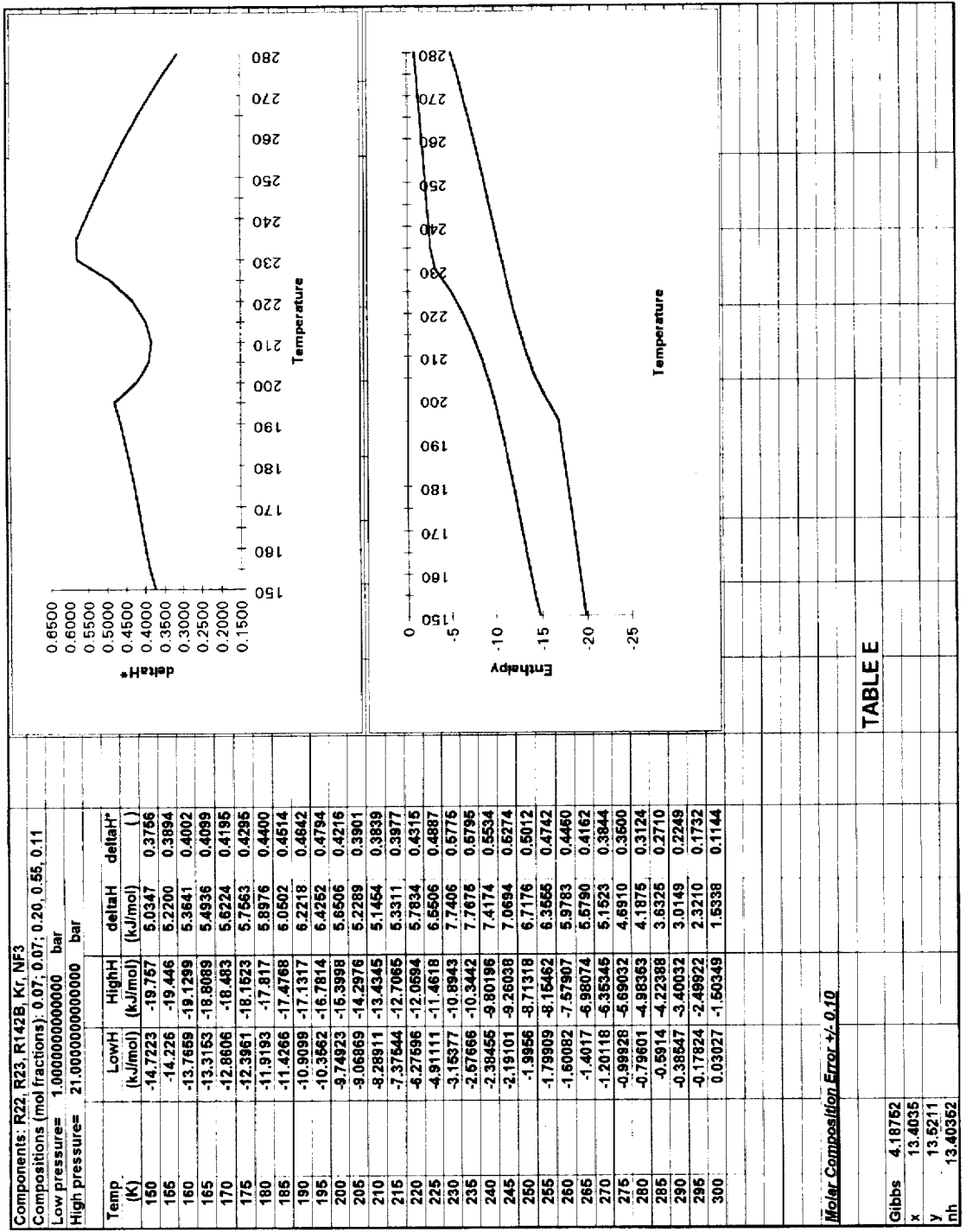
Figure 21:
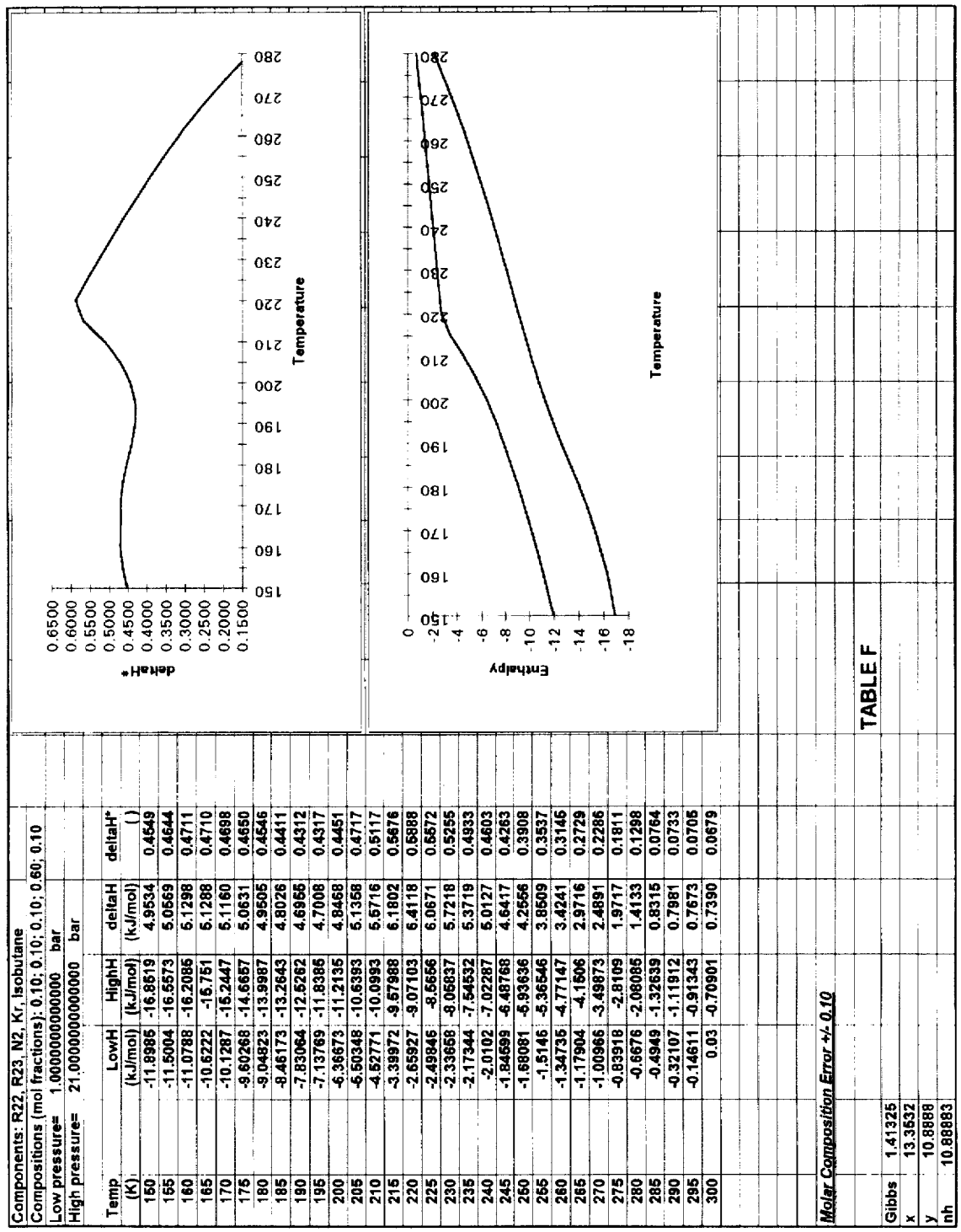
Figure 22:
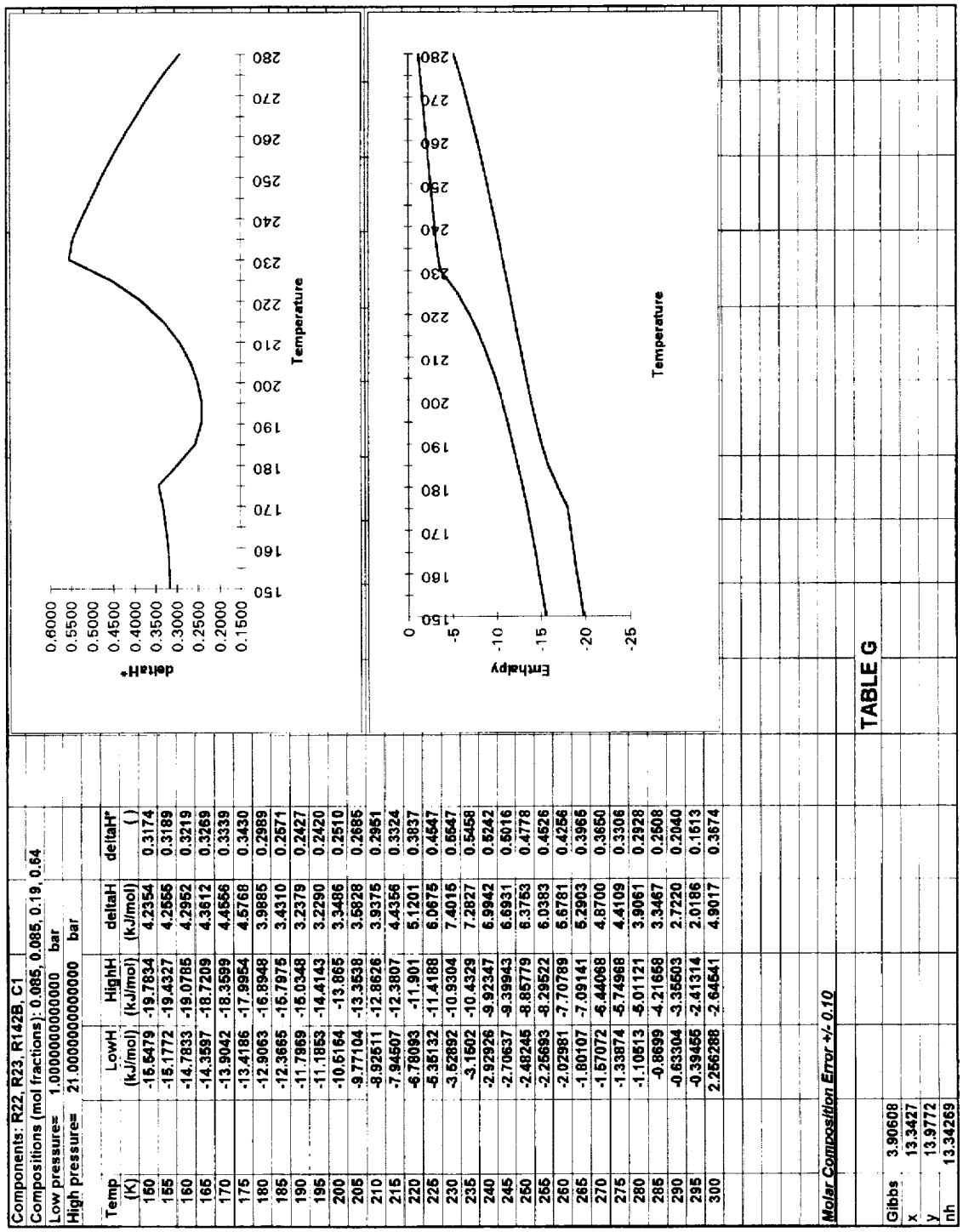
Figure 23:
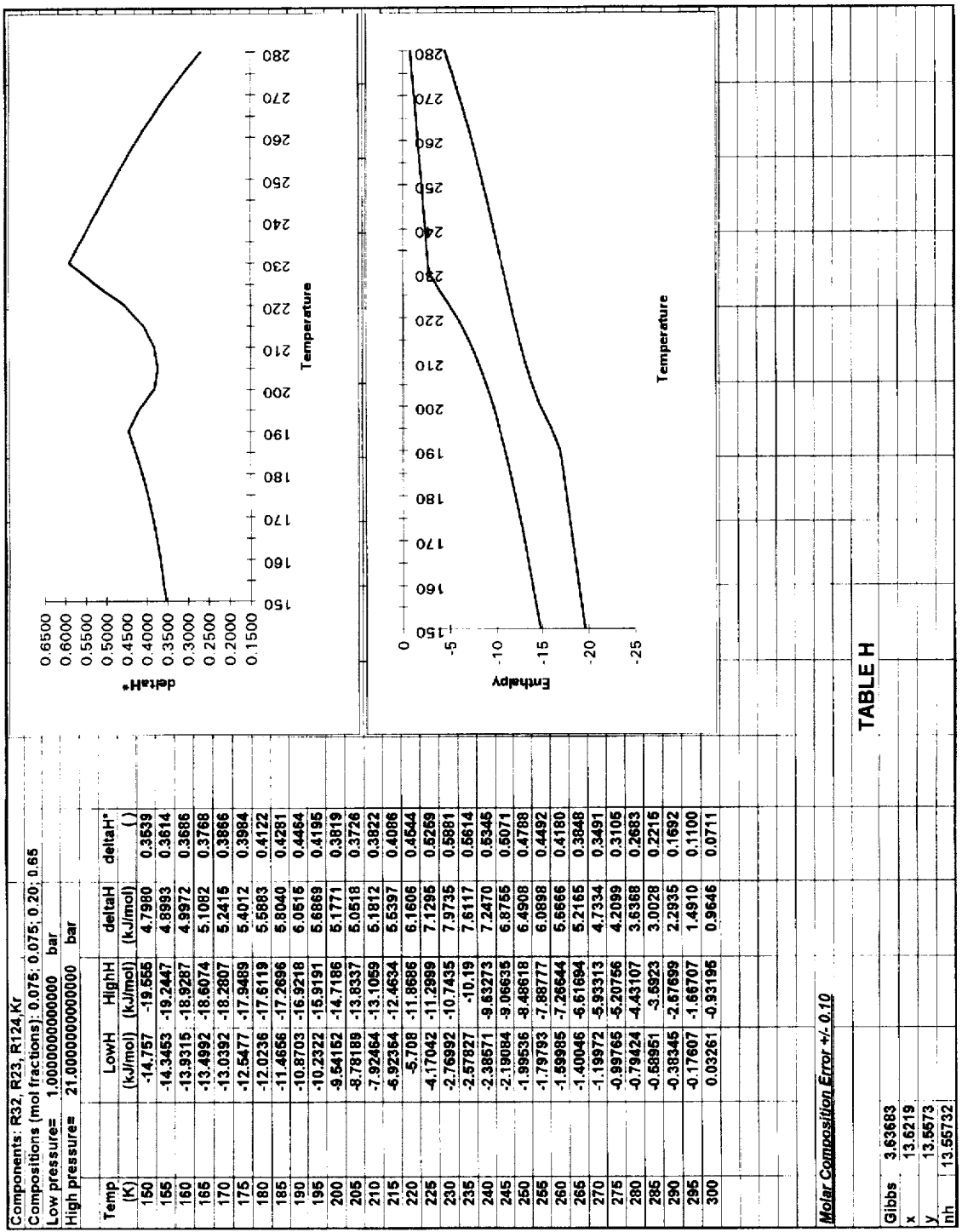
Figure 24:
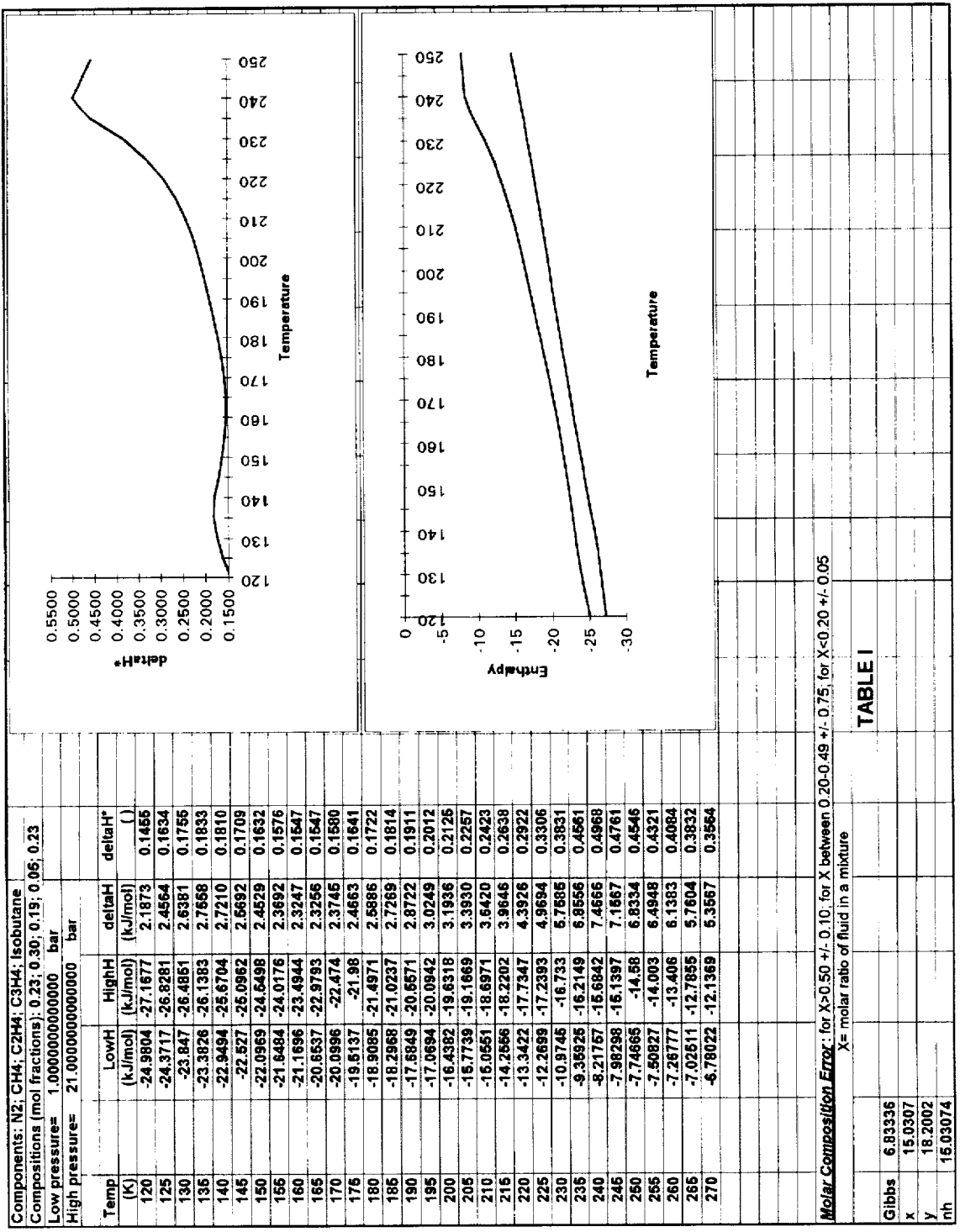
Figure 25:
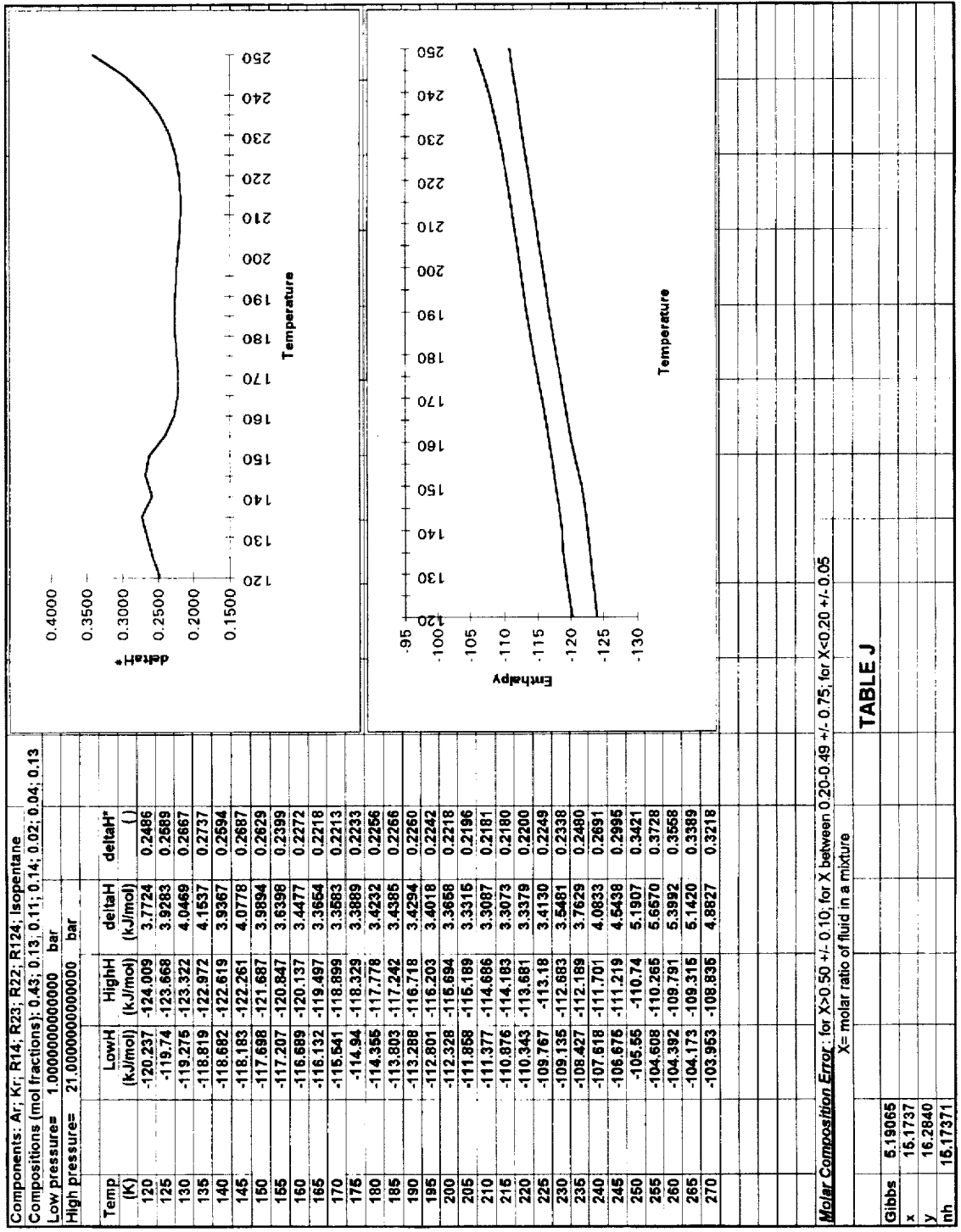
Figure 26:
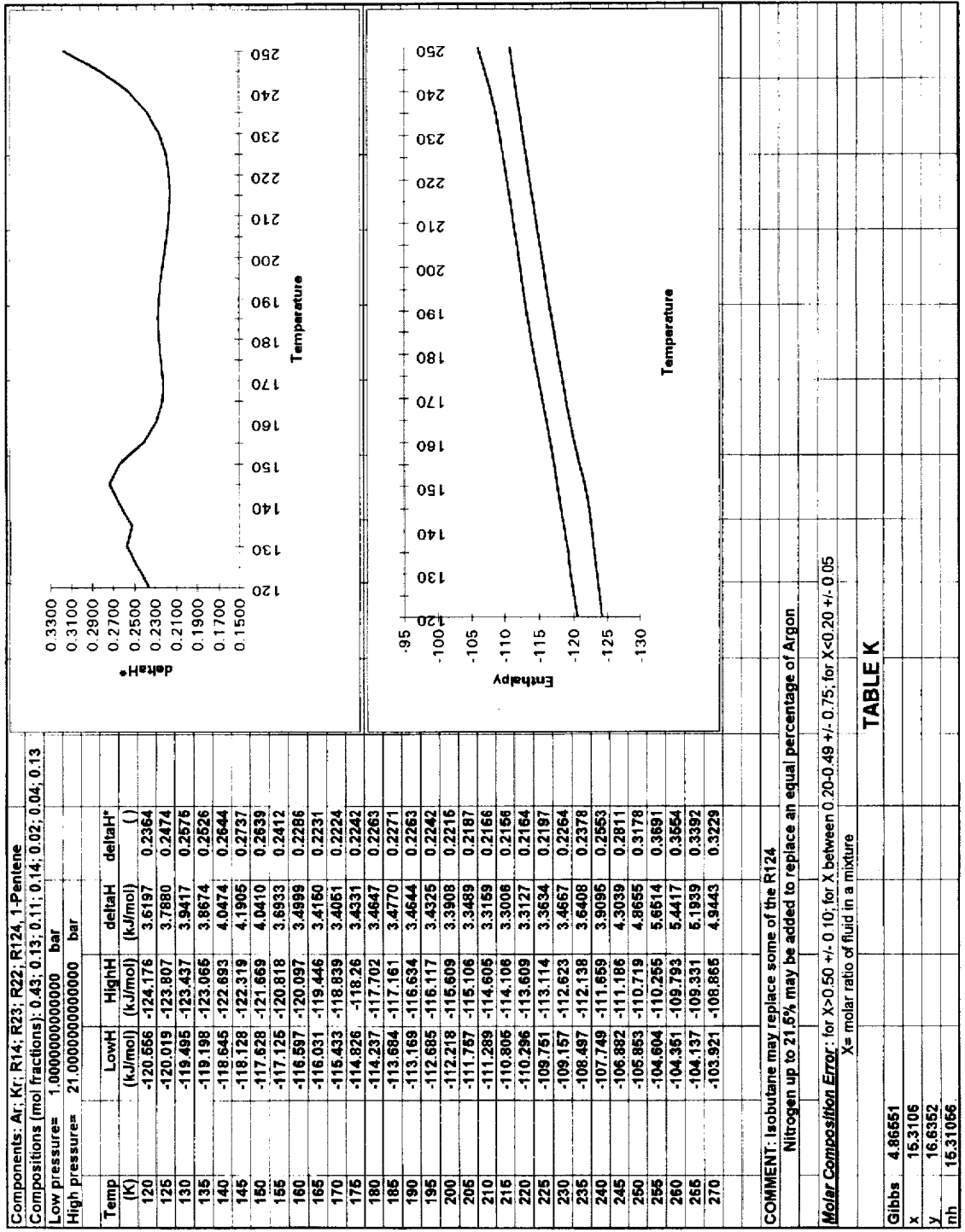
Figure 27:
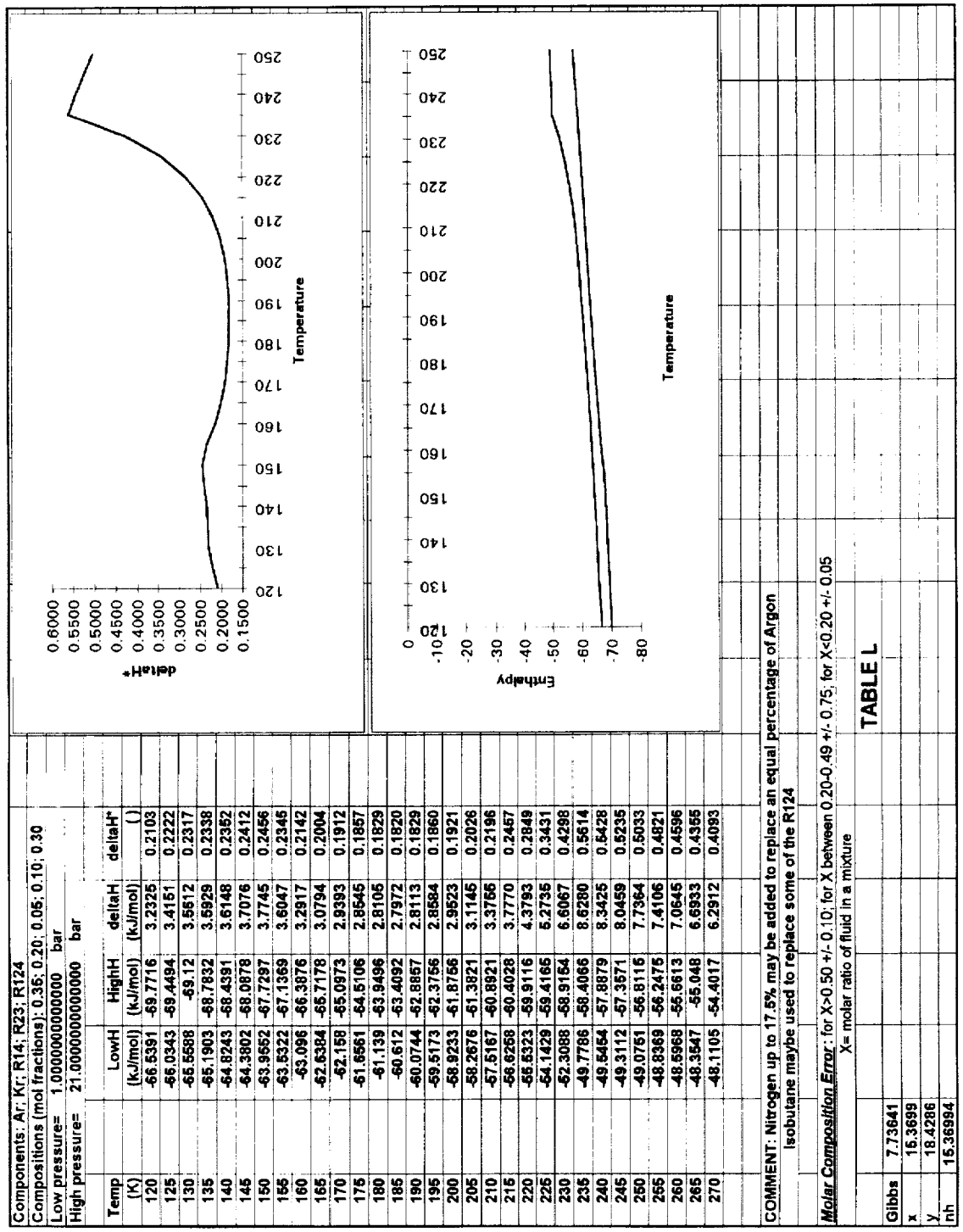
Figure 28:
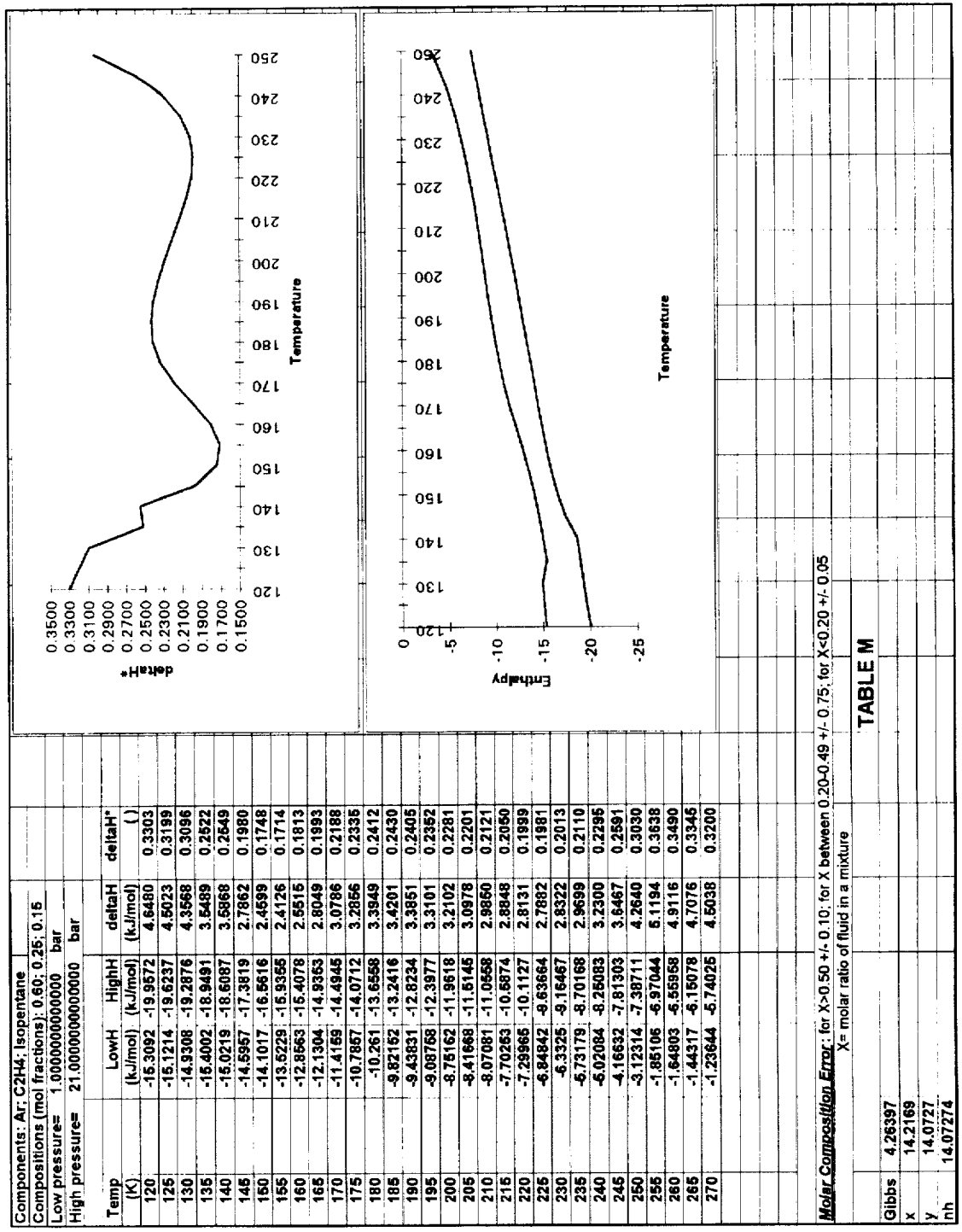
Figure 29:
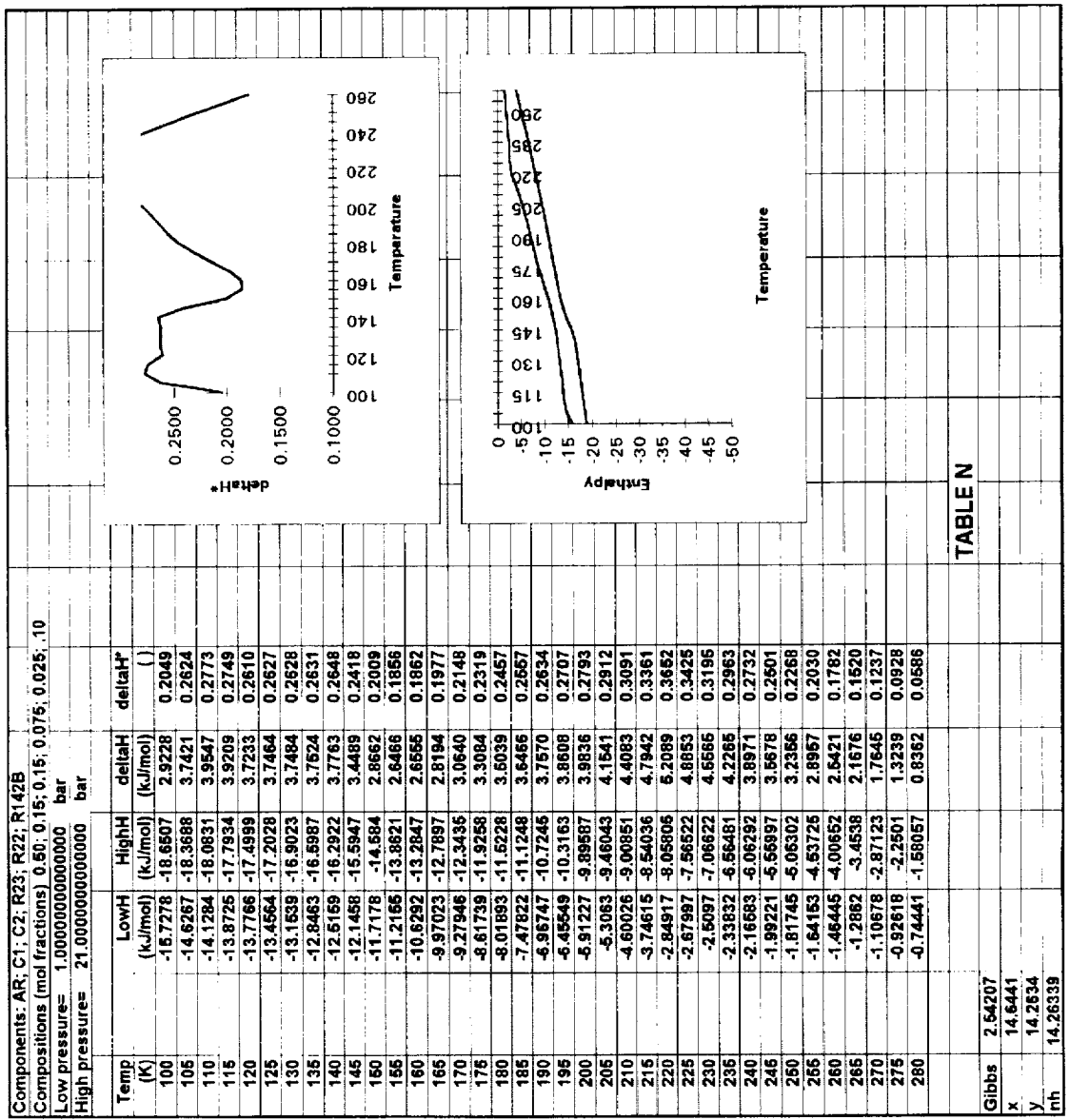
Figure 30:
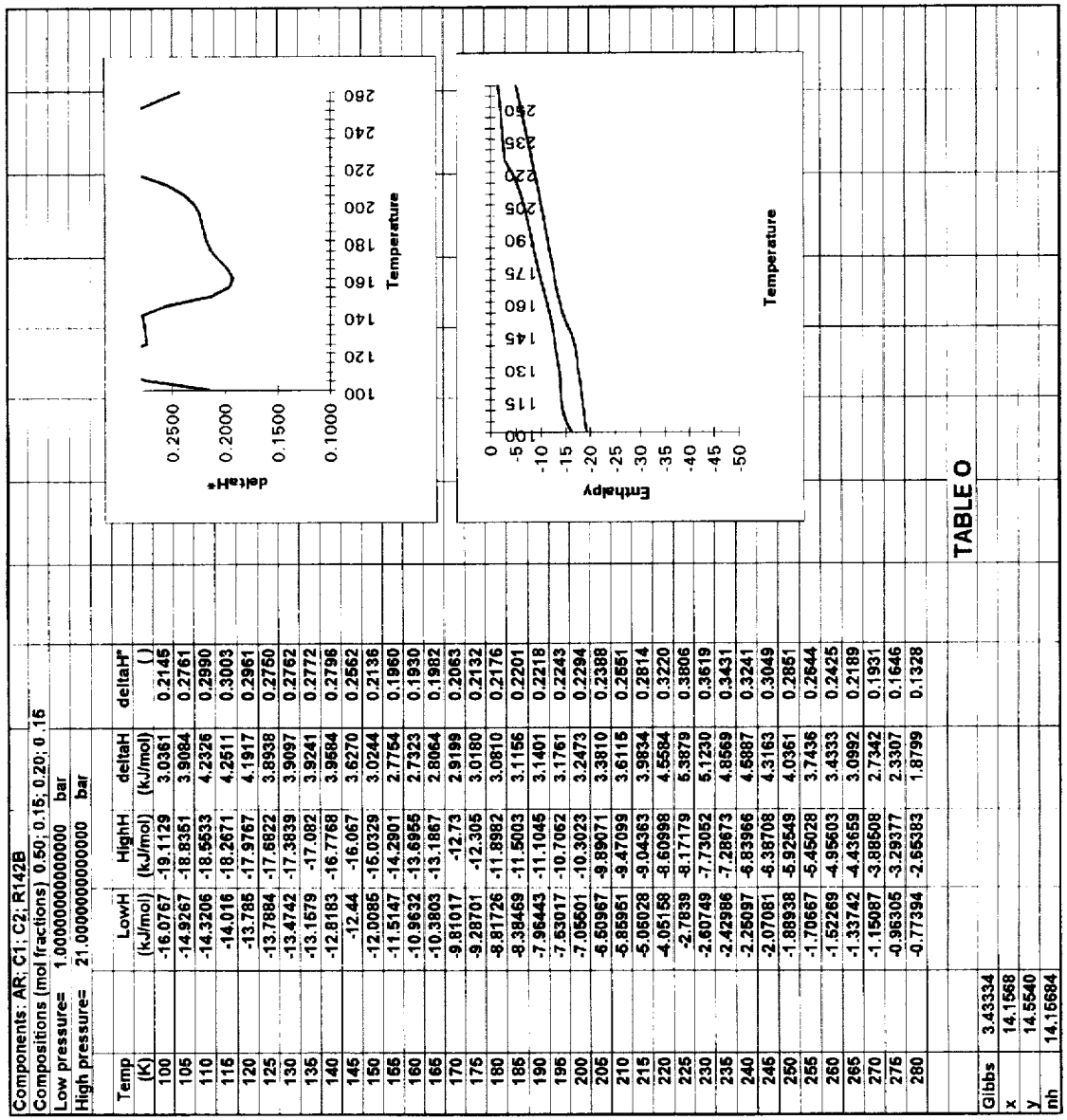
Figure 31:
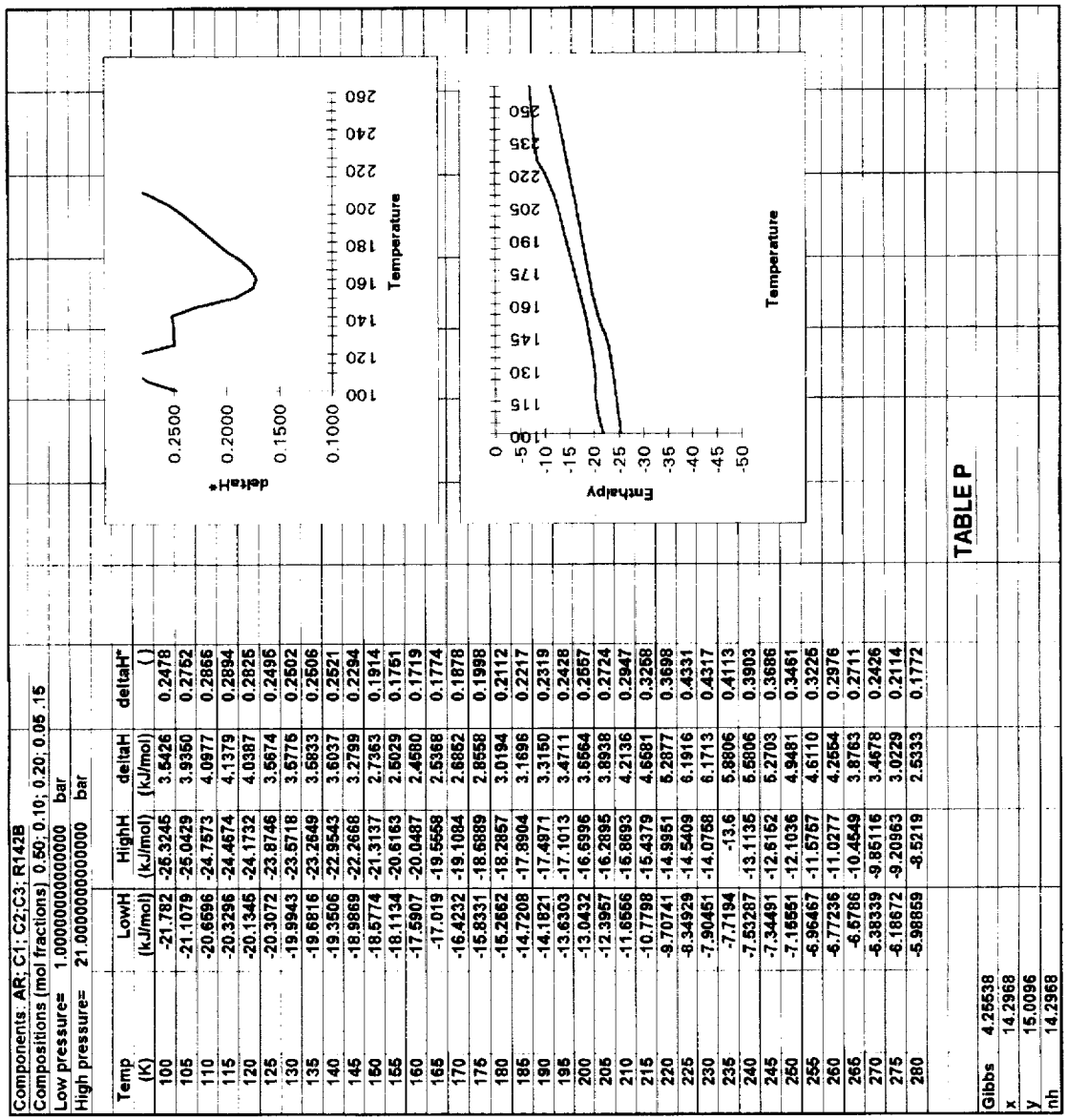
Figure 32:
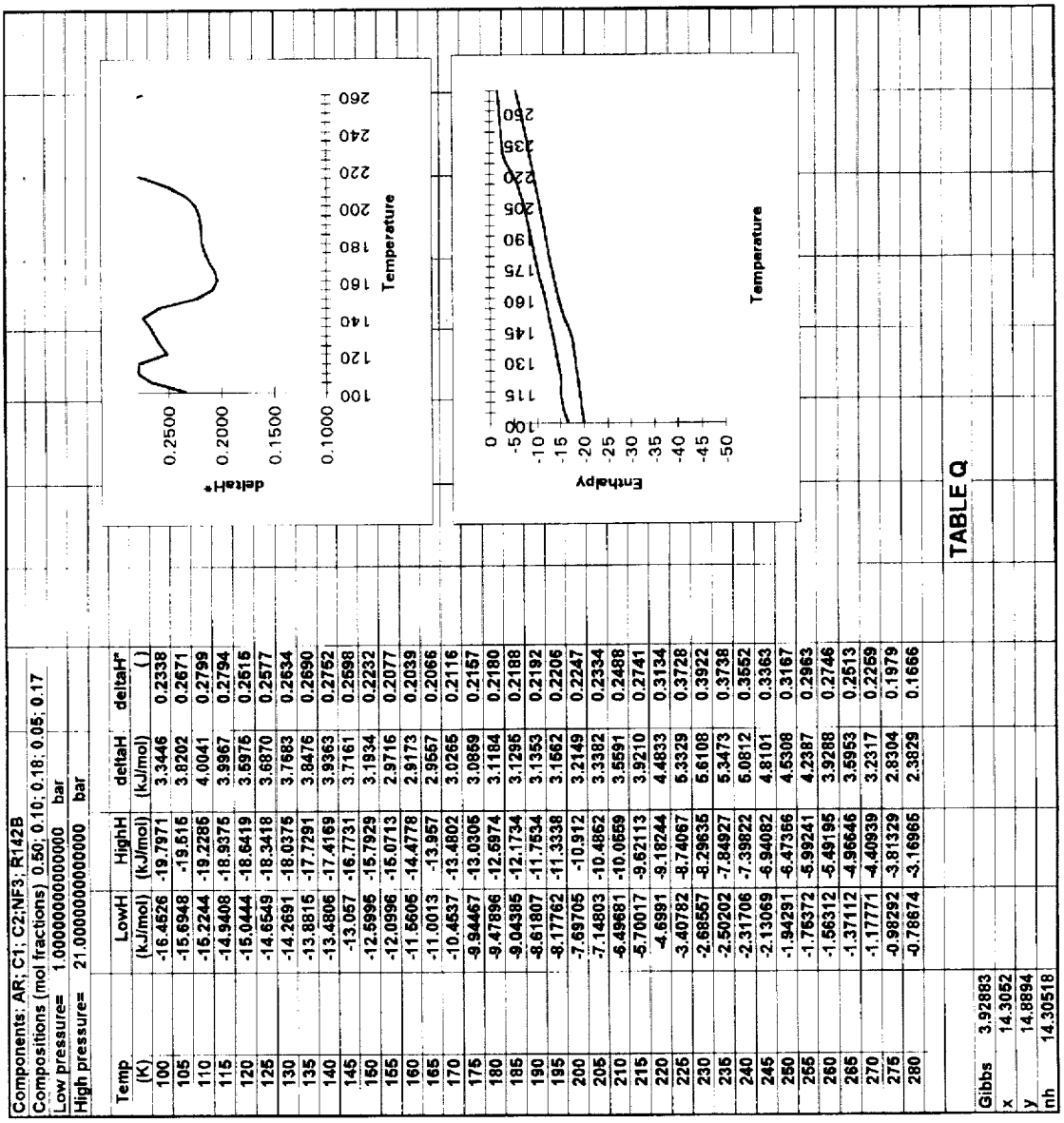

FIGS. 14 and 15 show a second embodiment of the distal end portion of the catheter 18', having a slender elongated heat transfer element 32'. This embodiment illustrates that the end portion of the catheter can have a fluid tube 27 affixed to the expansion element 30, a fluid chamber 29, and insulation 25 between the fluid chamber 29 and the extension tube 23. This construction insures that the cooling power is applied primarily through the heat transfer element 32'.

The size and inherent heat transfer capacity of the heat exchanger are limited, regardless of the design used. In the miniature environments envisioned for the use of this apparatus, space is at a premium. Whether used in a cardiac catheter or on a printed circuit board, therefore, severe size limitations will be placed upon the heat exchanger. For instance, a cardiac catheter must be introduced into, and maneuvered through a blood vessel to the target area for application of cooling. Therefore, a cardiac catheter necessarily is severely limited in diameter by the diameter of the blood vessels through which the catheter must pass. Further, the catheter must be highly maneuverable to be able to pass through the vascular system under the control of the physician. These maneuverability requirements call for the catheter to be somewhat flexible, especially near its tip, where the heat exchanger will be located. Unfortunately, most designs of the heat exchanger will probably be somewhat stiff, if not rigid. Therefore, the length of the heat exchanger must be severely limited, in order to leave the catheter in that region somewhat flexible. Limiting the size of the heat exchanger, of course, will result in a commensurate limitation of the amount of heat which can be transferred in the heat exchanger. This type of severe limitation on the size and capacity of the heat exchanger requires the overall refrigeration system to be kept at the highest possible level of performance by the selection of an optimum gas mixture. The optimun gas or fluid mixture will have thermodynamic properties which allow the system to perform cooling as well as possible, in spite of the size limitations. The goal of this fluid mixture selection process is to maximize the cooling power of the combination of the pre-cooling heat exchanger and the Joule-Thomson expansion element.

For any particular gas mixture, and for any selected pressure range and temperature range, there is a theoretical limit to the amount of heat which can be transferred, even in a perfect heat exchanger. That limit is given by the equation $$Q_{hx} = n[h(P,T_h) - h(P,T_c)]_{min}$$

where n is the molar flow rate, h is the molar enthalpy, $T_h$ is the temperature at the hot end of a heat exchanger, $T_c$ is the temperature at the cold end of the heat exchanger, and P is the pressure, with the value of $Q_{hx}$ being calculated at both the high pressure and the low pressure. The subscript $_{min}$ denotes the fact that the value of $Q_{hx}$ used is the lesser of the values computed at the two pressures.

Similarly, for that particular fluid mixture, and for that particular pressure and temperature range, there is a theoretical limit to the refrigeration power which can be achieved by even a perfect Joule-Thomson expansion element. That limit is given by the equation $$Q_r = n[h(P_l,T) - h(P_h,T)]_{min}$$

where $P_l$ is the low pressure, $P_h$ is the high pressure, and T is the temperature, with the value of $Q_r$ being calculated at a plurality of selected temperatures between the low and high temperatures at the extremes of the selected temperature range. The subscript $_{min}$ denotes the fact that the value of $Q_r$ used is the lowest of the values computed at the plurality of selected temperatures.

The ratio of the theoretical refrigeration power to the theoretical heat transfer capacity, or $Q_r/Q_{hx}$, can be thought of as a performance ratio which is characteristic of that particular fluid mixture, over that particular pressure and temperature range. The present invention includes a method for selecting a fluid mixture from among a group of candidate mixtures, which will have the highest performance ratio of any fluid mixture in the candidate group.

First, a list of pure component fluids is compiled, from which the candidate fluid mixtures will be formulated. Each component fluid might be an elemental fluid, or it could be a compound of several elements. Each component fluid might be either organic or inorganic. One requirement is that the fluid mixture must have a triple point below the lowest temperature in the selected temperature range, to prevent freezing of the fluid mixture in the apparatus. This requirement can be met by ensuring that each component fluid in the list has a triple point below the lowest temperature to be encountered. Alternatively, some of the component fluids can have triple points within the anticipated temperature range, as long as the triple point of each of the formulated fluid mixtures has a triple point below the anticipated temperature range. A second requirement is that each fluid mixture must have a positive Joule-Thomson coefficient; in other words, a pressure drop in the fluid mixture must be accompanied by a temperature drop. One way of ensuring this is to ensure that each of the component fluids on the list has a positive coefficient. Alternatively, some component fluids could have negative coefficients, as long as the coefficient of each fluid mixture has a positive coefficient.

For each of the component fluids in this list, the molar enthalpy must be known at a plurality of data points over the selected range of temperatures and the selected range of pressures, with these selected ranges being the temperature and pressure ranges at which the fluid mixture will be pumped through the refrigeration apparatus.

Then, a plurality of mixtures of the component fluids are selected, with each fluid mixture having a number of component fluids, and with each component fluid being present in a particular molar fraction. Any number of component fluids could theoretically be included in a fluid mixture. In actual practice, of course, computation capabilities will require that some limit be placed on the highest possible number of component fluids included in any one fluid mixture. Two fluid mixtures having the same component fluids, but with the component fluids being present in different molar fractions, would be considered two different fluid mixtures. As few as two candidate fluid mixtures might be selected for comparison in the simplest case. However, any number of mixtures might be formulated, up to the maximum number that can be formulated from the component fluids under consideration. Based upon the known thermodynamic properties of each of the component fluids, the molar enthalpy of each formulated fluid mixture is then calculated at a plurality of data points over the selected range of temperatures and the selected range of pressures.

One known method of calculating the molar enthalpy of each fluid mixture at a plurality of data points over the selected temperature and pressure ranges is the extended corresponding states method as used in the Mixture Property Database (DDMIX) program and the Thermophysical Properties of Hydrocarbon Mixtures (SUPERTRAPP) program, both available from the National Institute of Standards and Technology (NIST). Enthalpy values and other thermophysical properties of the candidate fluid mixtures can be estimated, with the aid of these programs, through the use of approximate shape factors based on saturation boundary matching. A reference fluid is typically selected, with the thermophysical properties of the other fluids being given in relation to the properties exhibited by the reference fluid. The refrigerant R134 has been found to serve as an appropriated reference fluid for these computations, but other fluids could also serve.

The component fluids selected must have a triple point below the low end of the selected temperature range, to eliminate the possibility of the formation of solids. The database of component fluids can contain refrigerants, light hydrocarbons including alkanes and alkenes, and noble gases, including argon, krypton, and neon. The phase split and enthalpy content of each selected candidate fluid mixture are computed as a function of temperature and pressure.

For each candidate fluid mixture, a series of calculations are then performed. It can sometimes be assumed that the pressure drop through the heat exchanger, on either the high pressure side or the low pressure side, is negligible. Alternatively, if an appreciable pressure drop is anticipated, a starting pressure can be selected which will take into account the pressure drop in the heat exchanger. For the low pressure in the selected pressure range, the molar enthalpy of the fluid mixture at the low temperature in the selected temperature range is subtracted from the molar enthalpy at the high temperature in the range, yielding a low pressure enthalpy difference between the fluid mixture states at the two temperatures. Similarly, for the high pressure in the selected pressure range, the molar enthalpy at the low temperature is subtracted from the molar enthalpy at the high temperature, yielding a high pressure enthalpy difference between the fluid mixture states at the two temperatures. The lesser of these two enthalpy differences is the theoretical molar enthalpy difference which could be achieved in a perfect counterflow heat exchanger operating with the selected fluid mixture over the selected temperature range and pressure range. The theoretical heat transfer capacity of such a heat exchanger with the selected fluid mixture, over the selected temperature and pressure range, is the product of the molar flow rate of the fluid mixture and this theoretical molar enthalpy difference. The theoretical heat transfer capacity is calculated for each candidate fluid mixture.

Then, a plurality of temperatures are selected at uniform increments over the selected temperature range. The number and size of the temperature increments can vary. A temperature increment of 5 degrees is often satisfactory. As an example, if the selected temperature range is from 120K to 270K, and if the size of the increment is set at five degrees, this results in a total of 30 increments, and 31 selected temperatures. For each candidate fluid mixture, the molar enthalpy of the fluid mixture at the high end of the selected pressure range is subtracted from the molar enthalpy at the low end of the pressure range, yielding a molar enthalpy difference between the fluid mixture states at the two pressures. This calculation is performed at each of the 31 selected temperatures. The higher the number of selected temperatures used, and the smaller the size of the increments, the greater will be the usefulness of the information calculated. The molar enthalpy difference calculated at each of these selected temperatures is the theoretical enthalpy increase which would occur during expansion of the candidate fluid mixture from the high pressure to the low pressure, at that temperature, if the temperature were to remain constant.

In Joule-Thomson expansion, however, there is very little or no opportunity for heat transfer to or from the fluid as it flows through the expansion element, no change in potential energy of the fluid, no work performed, and very little or no change in kinetic energy of the fluid. Therefore, the enthalpy states of the fluid before and after the expansion are essentially the same. As the pressure sharply decreases during expansion, the temperature of the fluid also sharply decreases, maintaining an essentially constant enthalpy. This colder fluid then can be used to cool the surroundings. In actuality, then, the temperature does not remain constant during expansion, and the theoretical refrigeration power available through Joule-Thomson expansion of the candidate fluid mixture, in the selected temperature range, is a function of the lowest theoretical enthalpy difference at any of the selected temperatures. More specifically, the theoretical refrigeration power available through Joule-Thomson expansion of the candidate fluid mixture is the product of the molar flow rate of the fluid mixture and the lowest theoretical molar enthalpy difference calculated at any temperature over the selected temperature range. The theoretical refrigeration power is calculated for each candidate fluid mixture.

Therefore, each candidate fluid mixture in the group exhibits a theoretical refrigeration power and a theoretical heat transfer capacity, over the selected temperature and pressure range. The ratio of the theoretical refrigeration power to the theoretical heat transfer capacity can be called a performance ratio which is characteristic of that particular fluid mixture over that temperature and pressure range. In order to optimize the operation of the apparatus of the present invention, a fluid mixture is chosen from among the candidate mixtures, which will result in the highest performance ratio. That is the optimum fluid mixture, among that group of candidates, within the temperature and pressure ranges selected. It can be seen that, if the performance ratio is equal to or greater than unity, meaning that the theoretical refrigeration power is as great as the theoretical heat transfer capacity, then the maximum cooling possible over the desired temperature and pressure range can be achieved through Joule-Thomson expansion alone, and no heat exchanger is needed. If the highest performance ratio in the group is less than unity, a heat exchanger will be required.

FIGS. 16 through 32 show Tables A through Q of enthalpy values of various fluid mixtures, derived through the extended corresponding states method. The component fluids used in formulating the candidate fluid mixtures were Ar, $CH_4$, $C_2H_4$, $C_3H_4$, Kr, $N_2$, $NF_3$, 1-pentene, Isobutane, Isopentane, Propylene, R14, R22, R23, R32, R124, and R142b. It has been found that various mixtures of these component fluids can be useful in the operation of miniature mixed gas refrigeration systems. The enthalpy values in each table are shown at a low pressure of 1.0 bar in the column labeled Low H, and at a high pressure of 21.0 bar in the column labeled High H. Based upon these enthalpy values, calculations are made to arrive at calculated values of delta H at each incremental temperature. Then, according to a method described below, based upon the selected temperature range, values of delta H* are calculated at each incremental temperature. In addition to the table of enthalpy and related values, each Figure also shows a graph of delta H* vs. temperature, and a graph of Low H and High H vs. temperature. Tables A through H show enthalpy values and delta H* between 150K and 300K, with the selected temperature range of interest being from 150K to 270K. Tables I through M show enthalpy values and delta H* between 120K and 270K, with the selected temperature range of interest being 120K to 270K. Tables N through Q show enthalpy values and delta H* between 100K and 280K, with the selected temperature range of interest being 100K to 260K.

The temperature ranges covered by the tables were arbitrarily selected to demonstrate that the enthalpy values for a mixture can be given over any desired temperature range, with the delta H* values in a given table being calculated based upon the selected temperature range of interest. Comparisons between fluid mixtures can be taken only from tables which have delta H* values calculated based on the same selected temperature range. For instance, all of the tables include enthalpy values over the range of 150K to 270K. However, only Tables A through H can be used for comparing calculated values of delta H* based upon a selected temperature range of 150K to 270K, because the values of delta H* in the other tables were calculated based upon a different selected temperature range.

Similarly, Tables I through Q all show enthalpy values over the range of 120K to 270K, but only Tables I through M can be used for comparing calculated values of delta H* based upon this selected temperature range. This is because the calculated values of delta H* in Tables N through Q were calculated based upon a selected temperature range of 100K to 260K. Listed values of delta H* which are outside the selected temperature range for a given table are calculated by the method of the present invention and shown in the table, but they are not pertinent to the selection of a fluid mixture for use within the selected temperature range.

The following discussion will specify selected temperature ranges which are covered by the tables referenced. In all cases, the temperature increments are 5 Kelvin degrees. H is molar enthalpy. The values of thermophysical properties are referenced to the values for R134a. Each table lists the molar enthalpy values of the candidate fluid mixture at increments of 5 degrees, for a low pressure of 1.0 bar, and for a high pressure of 21.0 bar. Further, for each incremental temperature over the range, a delta H is given, with delta H being the difference between the enthalpy values at the low pressure and the high pressure at that temperature.

For the low pressure, on a given table, it can be seen that the enthalpy value at the low temperature in the selected range can be subtracted from the enthalpy value at the high temperature in the selected range, to give a low pressure enthalpy difference. This is the y value shown near the lower left hand corner of the table. A similar calculation can be performed for the high pressure, yielding a high pressure enthalpy difference. This is the x value shown near the lower left hand corner. The lesser of the low pressure enthalpy difference and the high pressure enthalpy difference is the theoretical enthalpy difference available over that selected temperature range. This is the nh value shown near the lower left hand corner. The molar Gibbs free energy is also shown.

For each incremental temperature, if the value shown in the delta H column is divided by the theoretical enthalpy difference, nh, the result is shown in the column designated delta H*. Since the theoretical enthalpy difference, nh, is based upon a selected temperature range, the calculated values of delta H* are based upon that range, as well. The lowest value of delta H* within the selected temperature range, for any given table, is the same as the theoretical refrigeration power divided by the theoretical heat transfer capacity, since the molar flow rate is the same in both terms. This value, delta $H^*_{min}$, is the performance ratio for that fluid mixture, over the selected temperature range.

By way of example, select a temperature range of 120K to 270K, and a pressure range of 1.0 bar to 21.0 bar. Tables I through M contain delta H* values for five fluid mixtures over this selected temperature range. Over this selected temperature range, the fluid mixture having the highest value of delta $H^*_{min}$ is addressed in Table J, and the value of delta $H^*_{min}$ for that fluid mixture is 0.2180. This means that, of the fluid mixtures addressed in the tables which show calculated delta H* values based upon a selected temperature range of 120K to 270K, over this selected temperature and pressure range, the optimum fluid mixture is 43% Argon, 13% Krypton, 11% R14, 2% R22, 14% R23, 4%

R124, and 13% Isopentane. In Tables I through M, the molar composition values of 50% or higher have a possible error of +/−10%, values from 20% to 49% have a possible error of +/−7.5%, and values below 20% have a possible error of +/−5%.

By way of a further example, select a temperature range of 150K to 270K. Tables A through H contain delta $H^*$ values calculated for seven fluid mixtures based upon this range. For the fluid mixtures addressed in the tables which show calculated delta $H^*$ values over this range, the fluid mixture having the highest value of delta $H^*_{min}$ is addressed in Table E, and the value of delta $H^*_{min}$ for that fluid mixture is 0.3756. This means that, of the fluid mixtures addressed in these tables, over this selected temperature and pressure range, the optimum fluid mixture is 7% R22, 7% R23, 20% R142b, 55% Krypton, and 11% $NF_3$. In Tables A through H, the molar composition values have a possible error of +/−10%.

Use of the tables can be further illustrated by showing a means of eliminating toxicity or flammability in the selected gas mixture. Noting that $NF_3$ is potentially toxic to humans, for instance, the fluid mixture used in the last example may not be desirable for use in a mixed gas refrigeration system which will be used in a heart catheter. A fluid mixture which is similar, but which does not include this component fluid is addressed in Table C. It can be seen that the value of delta $H^*_{min}$ for that fluid mixture over the same selected temperature range is 0.3580. This means that, of the fluid mixtures addressed in these tables, over this selected temperature and pressure range, the optimum non-toxic fluid mixture is 7.5% R22, 7.5% R23, 20% R142b, and 65% Krypton. Toxicity or flammability can therefore be eliminated by a slight change in the gas mixture selected.

A still further use of the tables can be illustrated by considering the effect of pre-cooling the fluid mixture prior to feeding it to the micro-miniature heat exchanger. This can be done, for instance prior to introducing the fluid mixture into the catheter, by the use of a conventional, relatively large, heat exchanger. It can be seen that, for some of the fluid mixtures addressed in the tables, the minimum value of delta $H^*$ occurs in the upper part of the selected temperature range. For such a fluid mixture, pre-cooling of the fluid mixture can lower the top end of the temperature range to a level which results in a higher value of delta $H^*_{min}$ as the mixture flows through the expansion element.

For example, consider the possibility of using a pre-cooler to lower the temperature of the fluid mixture from 270K to 260K prior to introducing the mixture into the catheter. The mixture addressed in Table B will show a proportional increase in delta $H^*_{min}$ of over 40%, which is almost twice the proportional increase of over 20% which would result in the mixture addressed in Table D. Therefore, in systems where it is possible to pre-cool the fluid mixture before introducing it into the micro-miniature heat exchanger, and where it is desirable to use that pre-cooling to control the performance of the system, the mixture in Table B might be more advantageous.

It should be noted that gases with similar boiling points are interchangeable in a selected fluid mixture. For example, R124 can be substituted in the place of R142b or Isobutane, and Nitrogen can be substituted in the place of Argon. The substitution can be at an equal, or slightly different, percentage, with only slight changes in delta $H^*_{min}$. A good example of this can be seen by examining Tables C and H. The mixture in Table C is 7.5% R22, 7.5% R23, 20% R142b, and 65% Krypton, with a delta $H^*_{min}$ of 0.3580. In the mixture addressed in Table H, R32 has been substituted in place of R22, and R124 has been substituted in place of R142b, to arrive at an environmentally safer mixture, but the delta $H^*_{min}$ has only dropped to 0.3491, a drop of only about 2%.

While the particular invention as herein shown and disclosed in detail is fully capable of fulfilling the objects previously stated, it is to be understood that this disclosure is merely an illustration of the presently preferred embodiments of the invention and that no limitations are intended other than those described in the appended claims.

We claim:

1. A method for selecting a fluid mixture for use in a closed loop Joule-Thomson refrigeration system, said method comprising:

selecting a temperature range and a pressure range over which a closed loop Joule-Thomson refrigeration system will be operated;

selecting a plurality of component fluids, each said component fluid having known enthalpy values over said selected temperature range and said selected pressure range;

selecting a plurality of combinations of said component fluids to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture having the highest said performance ratio as the best performing fluid mixture for a closed loop Joule-Thomson refrigeration system over said temperature range and said pressure range.

2. A method for selecting a fluid mixture as recited in claim 1, further comprising substituting a replacement component fluid for one of said selected component fluids of said selected mixture, said replacement fluid having a boiling point substantially the same as the boiling point of said selected component fluid.

3. A method for selecting a fluid mixture as recited in claim 1, further comprising ensuring that each said selected fluid mixture has a triple point below said selected temperature range.

4. A method for selecting a fluid mixture as recited in claim 3, further comprising ensuring that each said component fluid has a triple point below said selected temperature range.

5. A method for selecting a fluid mixture as recited in claim 1, wherein said calculation of enthalpy values for each fluid mixture comprises comparing saturation boundaries of its respective said component fluids, to approximate saturation boundaries for said fluid mixture.

6. A method for selecting a fluid mixture as recited in claim 1, wherein said calculation of said theoretical heat transfer rate comprises:

subtracting a first enthalpy value of said fluid mixture, at a low end of said temperature range and a low end of said pressure range, from a second enthalpy value of said fluid mixture, at a high end of said temperature range and said low end of said pressure range, to yield a low pressure enthalpy difference;

subtracting a third enthalpy value of said fluid mixture, at said low end of said temperature range and a high end of said pressure range, from a fourth enthalpy value of said fluid mixture, at said high end of said temperature range and said high end of said pressure range, to yield a high pressure enthalpy difference; and multiplying the lesser of said low pressure enthalpy difference and said high pressure enthalpy difference by a selected flow rate of said fluid mixture, to yield said theoretical heat transfer rate.

7. A method for selecting a fluid mixture as recited in claim 1, wherein said calculation of said theoretical Joule-Thomson refrigeration power comprises:

subtracting a first enthalpy value of said fluid mixture, at a first selected temperature and a high end of said pressure range, from a second enthalpy value of said fluid mixture, at said selected temperature and a low end of said pressure range, to yield an enthalpy difference at said selected temperature;

repeating said subtraction of enthalpy values at a plurality of temperatures within said selected temperature range, to yield a plurality of enthalpy differences at said plurality of temperatures; and multiplying the lowest of said plurality of enthalpy differences by a selected flow rate of said fluid mixture, to yield said theoretical Joule-Thomson refrigeration power.

8. A method of operating a miniature refrigeration system, said method comprising:

providing a miniature closed loop refrigeration system having a compressor, a counterflow heat exchanger, and a Joule-Thomson expansion element;

selecting a pressure range of operation for a fluid mixture to be used in said closed loop refrigeration system, said pressure range having a high end no greater than 420 psia;

selecting a temperature range of operation for said fluid mixture to be used in said closed loop refrigeration system, said temperature range having a low end no greater than 183K;

selecting a plurality of component fluids, each said component fluid having known enthalpy values over said selected temperature range and said selected pressure range;

selecting a plurality of combinations of said component fluids to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each of said plurality of fluid mixtures;

selecting the fluid mixture having the highest performance ratio;

compressing said selected fluid mixture to said high end of said selected pressure range and a high end of said selected temperature range;

cooling said compressed fluid mixture in said heat exchanger; and isenthalpically expanding said fluid mixture in said expansion element from said high end of said selected pressure range to a low end of said selected pressure range, to cool said fluid mixture to said lower end of said selected temperature range.

9. A method of operating a miniature refrigeration system as recited in claim 8, further comprising ensuring that each said selected fluid mixture has a triple point below said selected temperature range.

10. A method of operating a miniature refrigeration system as recited in claim 8, wherein said calculation of enthalpy values for each fluid mixture comprises comparing saturation boundaries of its respective said component fluids, to approximate saturation boundaries for said fluid mixture.

11. A method of operating a miniature refrigeration system as recited in claim 8, wherein said calculation of said theoretical heat transfer rate comprises:

subtracting a first enthalpy value of said fluid mixture, at said low end of said temperature range and said low end of said pressure range, from a second enthalpy value of said fluid mixture, at said high end of said temperature range and said low end of said pressure range, to yield a low pressure enthalpy difference;

subtracting a third enthalpy value of said fluid mixture, at said low end of said temperature range and said high end of said pressure range, from a fourth enthalpy value of said fluid mixture, at said high end of said temperature range and said high end of said pressure range, to yield a high pressure enthalpy difference; and multiplying the lesser of said low pressure enthalpy difference and said high pressure enthalpy difference by a selected flow rate of said fluid mixture, to yield said theoretical heat transfer rate.

12. A method of operating a miniature refrigeration system as recited in claim 8, wherein said calculation of said theoretical Joule-Thomson refrigeration power comprises:

subtracting a first enthalpy value of said fluid mixture, at a first selected temperature and said high end of said pressure range, from a second enthalpy value of said fluid mixture, at said selected temperature and said low end of said pressure range, to yield an enthalpy difference at said selected temperature;

repeating said subtraction of enthalpy values at a plurality of temperatures within said selected temperature range, to yield a plurality of enthalpy differences at said plurality of temperatures; and multiplying the lowest of said plurality of enthalpy differences by a selected flow rate of said fluid mixture, to yield said theoretical Joule-Thomson refrigeration power.

13. A method for selecting a fluid mixture for use in a closed loop Joule-Thomson refrigeration system, said method comprising:

selecting a temperature range of 150K to 270K, and a pressure range of 1 bar to 21 bar, over which a closed loop Joule-Thomson refrigeration system will be operated;

selecting a plurality of combinations of component fluids from among the group Ar, $CH_4$, $C_2H_4$, $C_3H_4$, Kr, $N_2$, $NF_3$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 7% R22, 7% R23, 20% R142b, 55% Krypton, and 11% $NF_3$ as having the highest said performance ratio as the best performing fluid mixture possible, over said temperature range and said pressure range, among said fluid mixtures formulated from said component fluids, for use in said closed loop Joule-Thomson refrigeration system, wherein said molar percentages have a range of +/−10%.

14. A method for selecting a non-toxic fluid mixture for use in a closed loop Joule-Thomson refrigeration system, said method comprising:

selecting a temperature range of 150K to 270K, and a pressure range of 1 bar to 21 bar, over which a closed loop Joule-Thomson refrigeration system will be operated;

selecting a plurality of combinations of component fluids from among the group Ar, $CH_4$, $C_2H_4$, $C_3H_4$, Kr, $N_2$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 7.5% R22, 7.5% R23, 20% R142b, and 65% Krypton as having the highest said performance ratio as the best performing non-toxic fluid mixture possible, over said temperature range and said pressure range, among said fluid mixtures formulated from said component fluids, for use in said closed loop Joule-Thomson refrigeration system, wherein said molar percentages have a range of +/−10%.

15. A method for selecting an environmentally safe fluid mixture incorporating freons, for use in a closed loop Joule-Thomson refrigeration system, said method comprising:

selecting a temperature range of 150K to 270K, and a pressure range of 1 bar to 21 bar, over which a closed loop Joule-Thomson refrigeration system will be operated;

selecting a plurality of combinations of component fluids from among the group Ar, $CH_4$, $C_2H_4$, $C_3H_4$, Kr, $N_2$, $NF_3$, 1-pentene, Isobutane, Isopentane, Propylene, R14, R23, R32, and R124 to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 7.5% R32, 7.5% R23, 20% R124, and 65% Krypton as having the highest said performance ratio as the best performing environmentally safe fluid mixture possible, over said temperature range and said pressure range, among said fluid mixtures formulated from said component fluids, for use in said closed loop Joule-Thomson refrigeration system, wherein said molar percentages have a range of +/−10%.

16. A method for selecting a fluid mixture for use in a closed loop, pre-cooled Joule-Thomson refrigeration system, said method comprising:

selecting a temperature range and a pressure range over which a closed loop, pre-cooled Joule-Thomson refrigeration system will be operated;

selecting a plurality of combinations of component fluids to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture;

selecting the fluid mixture having the highest said performance ratio;

selecting a revised temperature range having an upper limit below the boiling point of one of said component fluids used in said selected fluid mixture;

eliminating said component fluid having said boiling point above said upper limit of said revised temperature range, to derive a revised fluid mixture as the best performing fluid mixture possible, among said fluid mixtures formulated from said component fluids, for use in said closed loop, pre-cooled Joule-Thomson refrigeration system, wherein said revised mixture is pre-cooled to said upper limit of said revised temperature range.

17. A method for selecting a fluid mixture for use in a closed loop, pre-cooled Joule-Thomson refrigeration system, said method comprising:

selecting a temperature range of 150K to 270K, and a pressure range of 1 bar to 21 bar, over which a closed loop, pre-cooled Joule-Thomson refrigeration system will be operated;

selecting a plurality of combinations of component fluids from among the group Ar, $CH_4$, $C_2H_4$, $C_3H_4$, Kr, $N_2$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 7.5% R22, 7.5% R23, 20% R142b, and 65% Krypton as having the highest said performance ratio;

selecting a revised temperature range of 150K to 245K having an upper limit below the boiling point of R142b; and eliminating R142b from said selected fluid mixture, to derive the revised fluid mixture 20% R22, 20% R23, and 60% Krypton, for use in said closed loop, pre-cooled Joule-Thomson refrigeration system, wherein said revised mixture is pre-cooled to 245K, wherein said molar percentages have a range of +/−10%.

18. A method for selecting a fluid mixture for use in a closed loop, pre-cooled Joule-Thomson refrigeration system, said method comprising:

selecting a temperature range of 150K to 270K, and a pressure range of 1 bar to 21 bar, over which a closed loop, pre-cooled Joule-Thomson refrigeration system will be operated;

selecting a plurality of combinations of component fluids from among the group Ar, $CH_4$, $C_2H_4$, $C_3H_4$, Kr, $N_2$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 7.5% R22, 7.5% R23, 20% R142b, and 65% Krypton as having the highest said performance ratio;

selecting a revised temperature range of 150K to 245K having an upper limit below the boiling point of R142b; and eliminating R142b from said selected fluid mixture, to derive the revised fluid mixture 25% R22, 25% R23, and 50% Krypton, for use in said closed loop, pre-cooled Joule-Thomson refrigeration system, wherein said revised mixture is pre-cooled to 245K, wherein said molar percentages have a range of +/−10%.

19. A method for selecting a fluid mixture for use in a closed loop Joule-Thomson refrigeration system, said method comprising:

selecting a temperature range of 120K to 270K, and a pressure range of 1 bar to 21 bar, over which a closed loop Joule-Thomson refrigeration system will be operated;

selecting a plurality of combinations of component fluids from among the group Ar, $CH_4$, $C_2H_4$, $C_3H_4$, Kr, $N_2$, $NF_3$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 43% Ar (+/−7.5%), 13% Kr (+/−5%), 11% R14 (+/−5%), 2% R22 (+/−5%), 14% R23 (+/−5%), 4% R124 (+/−5%), and 13% Isopentane (+/−5%) as having the highest said performance ratio as the best performing fluid mixture possible, over said temperature range and said pressure range, among said fluid mixtures formulated from said component fluids, for use in said closed loop Joule-Thomson refrigeration system.

20. A method for selecting a fluid mixture for use in a closed loop Joule-Thomson refrigeration system, said method comprising:

selecting a temperature range of 100K to 260K, and a pressure range of 1 bar to 21 bar, over which a closed loop Joule-Thomson refrigeration system will be operated;

selecting a plurality of combinations of component fluids from among the group Ar, $CH_4$, $C_2H_4$, $C_3H_4$, Kr, $N_2$, $NF_3$, 1-pentene, Isobutane, Isopentane, Propylene, R14, R22, R23, R32, R124, and R142b to formulate a plurality of fluid mixtures;

calculating enthalpy values for each said fluid mixture at a plurality of data points over said temperature range and said pressure range;

calculating a theoretical heat transfer rate achievable in a counterflow heat exchanger with each said fluid mixture, over said selected temperature and pressure range;

calculating a theoretical Joule-Thomson refrigeration power achievable with each said fluid mixture, over said selected temperature and pressure range;

calculating a performance ratio of said theoretical refrigeration power to said theoretical heat transfer rate, for each said fluid mixture; and selecting the fluid mixture 50% Ar (+/−10%), 10% $CH_4$ (+/−5%), 18% $C_2H_4$ (+/−5%), 5% $NF_3$ (+/−5%), and 17% R142b (+/−5%) as having the highest said performance ratio as the best performing fluid mixture possible, over said temperature range and said pressure range, among said fluid mixtures formulated from said component fluids, for use in said closed loop Joule-Thomson refrigeration system.

* * * * *